(12) United States Patent
Ogle et al.

(10) Patent No.: US 8,728,817 B2
(45) Date of Patent: May 20, 2014

(54) COMPOSITIONS AND METHODS FOR MAKING AND USING LAMININ NANOFIBERS

(75) Inventors: Roy Clinton Ogle, Norfolk, VA (US); Edward A. Botchwey, III, Charlottesville, VA (US); Rebekah A. Neal, Cambridge, MA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 270 days.

(21) Appl. No.: 13/045,095

(22) Filed: Mar. 10, 2011

(65) Prior Publication Data

US 2011/0236974 A1    Sep. 29, 2011

Related U.S. Application Data

(63) Continuation-in-part of application No. 12/598,776, filed as application No. PCT/US2008/062395 on May 2, 2008, now abandoned.

(60) Provisional application No. 61/312,695, filed on Mar. 11, 2010, provisional application No. 60/927,583, filed on May 4, 2007.

(51) Int. Cl.
*C12N 5/0793* (2010.01)
*C07K 14/00* (2006.01)

(52) U.S. Cl.
USPC .................. 435/398; 514/17.7; 977/795

(58) Field of Classification Search
None
See application file for complete search history.

(56) References Cited

PUBLICATIONS

Evans, G.,"Peripheral Nerve Injury: A review and approach to tissue engineering constructs", The Anatomical Record 263: 396-404 (2001).*

* cited by examiner

*Primary Examiner* — Anand Desai
(74) *Attorney, Agent, or Firm* — Rodney L. Sparks

(57) ABSTRACT

The present invention provides methodologies and parameters for fabrication of the hybrid biomaterial by blending pure laminin or complex extracts of tissues containing laminin with biopolymers such as polycaprolactone (PCL), polylactic/polyglycolic acid copolymer (PLGA) or Polydioxanone (PDO) in fluoroalcohols (HFP, TFA), fabrication of substrates and scaffolds and devices from the hybrid biomaterial in forms such as films, nanofibers by electrospinning or microspheres, and the biological or biomedical use of the material or devices derived from it.

25 Claims, 22 Drawing Sheets

C

D

E

F

C

D

COMPOSITIONS AND METHODS FOR MAKING AND USING LAMININ NANOFIBERS

CROSS REFERENCE TO RELATED APPLICATIONS

This application is entitled to priority pursuant to 35 U.S.C. §119(e) to U.S. provisional patent application No. 61/312,695, filed on Mar. 11, 2010, and is a continuation-in-part of U.S. patent application Ser. No. 12/598,776, filed on Nov. 4, 2009, which is entitled to priority to International App. No. PCT/US2008/062935, which is entitled to priority to U.S. provisional patent application No. 60/927,584, filed on May 4, 2007, the entireties of which are incorporated by reference herein.

STATEMENT REGARDING FEDERALLY SPONSORED RESEARCH OR DEVELOPMENT

This invention was supported by Grant No. DE-010369-08 awarded by the National Institutes of Health and Grant No. 736002 awarded by the National Science Foundation. The United States Government therefore has certain rights in the invention.

FIELD OF THE INVENTION

The present invention relates to compositions, methods, and apparatuses for preparing and using electrospun protein-polymer mixtures.

BACKGROUND

Laminins are a family of large extracellular matrix (ECM) proteins found primarily in basement membranes associated with all epithelial, endothelial, muscle, fat and Schwann cells. The laminins serve critical functions in cell attachment, growth, migration, and differentiation of many cell types. Laminin I is the first extracellular matrix protein to appear during embryonic development, where it surrounds the inner cell mass of the compacted blastocyst. Studies of laminin I purified from the Engelbreth-Holm-Swarm (EHS) tumor established that laminin is required for cell attachment and growth, and many studies confirm the importance of laminins in development and survival. Laminin interacts with cells through a variety of integrins, the dystroglycan receptor, syndecan, and other type receptors broadly expressed on many cell types.

Extracellular matrix (ECM) provides the extracellular environment for almost all mammalian cell types. It is composed of structural proteins such as collagen and elastin, proteoglycans, and proteins such as fibrin, fibronectin, and laminin. One of the over-reaching goals of cell biology and tissue engineering is to recreate the extracellular environment a cell experiences in vivo, and attaining the appropriate ECM components in appropriate morphological and physical characteristics is of the utmost importance.

Peripheral nerve transection occurs commonly in traumatic injury, causing motor and sensory deficits distal to the site of injury. Transection requires appropriate surgical intervention to maximize retention of function and sensation [1]. Reanastomosis by direct suture of the severed nerve fiber endings through the perineurium is the gold standard and results in the best surgical outcome; however, when the nerve retracts after injury and tensionless repair is impossible, cable grafts are often used. Cable grafting takes short nerve segments from a donor nerve and directly reapposes a series of grafts to fill the nerve gap without tension [2]. This procedure leaves deficits at the donor site, and is variably less successful at recovering function at the injury site. To help alleviate donor site morbidity, increased operative time, and size mismatch of the donor nerve, clinicians may choose a nerve conduit for repair of sensory nerves. Conduits currently on the market are biocompatible, biodegradable, hollow tubes into which the nerve ends are sutured. These conduits serve as only an empty, isolated space for growth. Regeneration through nerve conduits typically provides an improvement over no treatment, but for long defects ($\geq 10$ mm), conduits often fail due to lack of structural support over the time required for the axon to traverse the gap distance [3].

When axons remain without connection to their target tissue over significant periods of time they lose the ability to regenerate, and the possibility for functional recovery is lost. A decline in the regenerative capacity of both axons and Schwann cells, the support cells of the PNS, begins in humans approximately eight weeks after injury. At six months to one year, regeneration is much less likely [4]. This knowledge of the degeneration and regeneration processes has led researchers to the conclusion that, to outperform autografts and allografts, conduits must provide structural support to regenerating axons [5]. To facilitate increased speed of regeneration, in addition to physical support and guidance, the ideal conduit would also provide biochemically relevant signals to guide axonal outgrowth, thus playing an active role in peripheral nerve regeneration.

Multiple strategies exist for improving repair and regeneration with nerve conduits. These involve optimization of cellular components, extracellular matrix proteins, and soluble factors. As occurs in vivo, the presence of any one of these three can cause generation of the other two. Extracellular matrix proteins not only present appropriate and recognizable surfaces for interactions such as cell binding and migration, but are able to be manipulated and remodeled by cells to match a more uninjured milieu. Utilizing extracellular matrix components allows for natural cell-matrix interactions to occur such as ligand binding, process guidance, and regeneration, as the substrate can drive cell-fate decisions [6]. These cell-fate decisions in vivo are driven by interactions with the dynamic tissue matrix within the extracellular environment.

Electrospun laminin nanofibers can function as a basement membrane mimetic material, both in terms of geometry and composition, driving attachment, differentiation, and process extension of neuron-like or neuronal precursor cells [7]. Electrospinning is an ideal technology to create implantable 3-D scaffold conduits for peripheral nerve regeneration. The resulting isotropic randomly oriented nanofibrous mesh, or anisotropic aligned nanofibrous mesh will provide the necessary structural support and high surface area to volume ratios to facilitate cell migrations required to bridge peripheral nerve to aid in regeneration. Other groups, notably Bellamkonda and colleagues [3,8,9] have filled conduits with thin films of synthetic polymer fibers and found this physical support for outgrowth, along with directional guidance through fiber alignment, support regeneration and functional recovery across long gaps (>10 mm).

There is a long felt need in the art to recreate an extracellular environment to aid in cellular and tissue processes such as attachment, migration, and wound healing. More specifically, there is a need to create such an environment to enhance nerve regeneration. The present invention satisfies these needs.

SUMMARY OF THE INVENTION

The present invention encompasses methodologies and parameters for the formation of nanofibrous (to microfibrous) protein-polymer mixtures via electrospinning. The present invention further encompasses uses of the resulting nanofibers comprising laminin and a polymer. In one aspect, the laminin is laminin I. In one aspect, the polymer is PCL.

The present invention provides large cost savings over other techniques. The cost of laminin and reconstituted basement membrane (RBM) manufacture is extremely high and approaches being prohibitive in its usage as a three-dimensional scaffold, such as nanofiber meshes. The present invention provides a mixture of at least one synthetic polymer and at least one extracellular matrix protein, thus decreasing the costs for preparing the mixed nanofiber of the invention because less protein is needed. In one aspect, the synthetic polymer is PCL. In one aspect, the extracellular matrix protein is laminin. In one aspect, the laminin is laminin I.

It is also desirable to increase the tensile strength of laminin-rich materials and reduce their stickiness to electrodes and molds during manufacture. To achieve these improvements, methods are disclosed herein to fabricate co-spun laminin and synthetic biodegradable polymer materials that can be fabricated into nanofiber meshes, films, and microspheres among a broad variety of possible biomedical applications. The synthetic polymer provides a better base for encapsulation of drugs and growth factors, a mechanically stable substrate with defined decay rates, and a platform for manipulating fiber morphology and geometry, while serving as a low cost filler to reduce the amount of laminin necessary. The applications for this protein-polymer electrospun mixture will dramatically increase as the cost of manufacture decreases and the repeatability increases. The electrospun nanofibers can be applied in culture, device fabrication for tissue engineered constructs, conduits, or even as a bandage, or component thereof, or other topical application.

Laminin, which contains many biologically active moieties (including a moiety having a sequence consisting of an isoleucine, a lysine, a valine, an alanine, and another valine), may especially benefit from orientation at the individual molecule level in a nanofiber mesh. Providing the biologically active molecule laminin within the framework of intraluminal nanofiber scaffold may improve axonal guidance and support during regeneration.

Because administration of laminin can cause problems to a subject, particularly if it enters the bloodstream, where the laminin may elicit an immune response, being able to use less laminin to prepare the nanofibers of the invention is extremely beneficial to the health of the patient.

The present invention further provides compositions and methods for aligning the laminin-polymer nanofiber mixtures of the invention. In addition to the physical benefit of providing an aligned substrate for directional outgrowth, there exist two further potential benefits of aligned nanofibers for peripheral nerve regeneration, both occurring as a result of the electric field changes created by the insulting gap. First, high field forces at the edges of the gap exert stronger forces on individual polymer fibers, causing fibers to stretch across the gap, decreasing their resulting diameter. The ideal conditions for alignment and stretching have been explored by our collaborators in a recent publication [10]. This stretching effect decreases the lower bound of mean fiber diameters below 100 nm, yielding fiber diameters mimetic of the natural basement membrane, which has feature sizes in the range of 75-150 nm [11]. Second, fiber alignment across two electrodes separated by an insulating gap results in molecular level orientation of individual polymer molecules within the fiber [12].

The present application discloses conditions and appropriate parameters to synthesize nanofibers comprising mixtures of at least one protein and at least one polymer, wherein the nanofibers range in size from a diameter of about 10 nM to a diameter of over 1,000 nM via electrospinning. Many applications in biology and medicine can be based on the protein-polymer nanofibers or mesh resulting from this procedure. The methodologies described herein are useful for numerous tissue engineering applications, as laminin is an essential component of the ECM for many cell types in various tissues. For example, laminin is known to be a major migratory/extension surface for the axons of neurons during development and peripheral nerve healing. Conduits composed of, or lined with, laminin-polymer nanofibers are provided herein for tissue engineering constructs to mediate peripheral nerve regeneration. Additionally, cell types that normally reside on basement membranes can be delivered on constructs based on laminin-polymer nanofibers.

While a vast literature documents the importance and activity of laminin, and several labs have shown success with recreating the fibrous morphology of collagen in the laboratory using electrospinning techniques, we have discovered appropriate parameters to achieve nanofibers comprising a mixture of laminin and at least one polymer via electrospinning. The materials fabricated by this process may be used as an anhydrous coating of scaffold biomaterials for tissue engineering, as well as substrate for ex vivo cultivation of both specialized tissue cells and stem cells. The latter could be a tremendous aid to basic science research as differentiation and phenotype expression of cells on biomimetic laminin blend scaffolds may be more representative of in vivo behavior. Because other proteins, such as collagen, have been used to form meshes and have been subjected to electrospinning, the present invention encompasses the use of not just laminin, but other proteins as well.

The laminin-polymer nanofibers of the invention are useful, inter alia, for:

1) A scaffold for stimulating or enhancing regeneration and healing of numerous injured or diseased tissues such as injured or diseased nerves and bone, including, through delivery of stem cells or promotion of endogenous healing.

2) A biomimetic coating of scaffold materials to enhance or control cell-material interactions both in vitro and in vivo 3) An anhydrous base membrane scaffold for cell cultivation and basic science research, including a potential media for cultivation of undifferentiated embryonic stem cells in place of feeder layers.

4) A model basement membrane barrier for migration and invasion studies in vitro.

The nanofibers comprising a mixture of laminin and at least one synthetic polymer prepared by the methods of the invention should have a very long shelf life when stored with desiccation. They have far greater tensile strength than matrigel gels. The nanoscale fibers are similar to the fibers seen by cells encountering laminin in real basement membranes, thus they may be expected to demonstrate novel biomimetic effects. The materials fabricated by this process may, for example, be used as an anhydrous coating of scaffold biomaterials for tissue engineering, as well as substrate for ex vivo cultivation of both specialized tissue cells and stem cells. The latter could be a tremendous aid to basic science research as differentiation and phenotype expression of cells on biomimetic laminin scaffolds may be more representative of in vivo behavior.

Due to the sensitivity of nanofibers comprising laminin, glutaraldehyde crosslinking may destroy the bioactivity of the laminin protein. The present invention provides compositions and methods for electrospun laminin which do not have to be crosslinked. In one aspect, the solvent HFP is used and laminin activity remains, and no cross-linking is required.

The present invention further provides compositions and methods for varying the diameter of the protein-polymer mixture nanofibers. In one aspect, the protein is laminin. In one aspect, the polymer is PCL.

In one embodiment, the present invention provides a method of preparing electrospun nanofibers comprising: obtaining purified protein, dissolving the purified protein in HFP, obtaining at least one synthetic polymer and dissolving it in the HFP, loading the dissolved protein-polymer mixture into a dispensing container comprising a positive lead, subjecting the lead to a driving voltage from a power supply, pumping the protein-polymer mixture dissolved in HFP through an opening in the dispensing container, and collecting the laminin-polymer mixture dissolved in HFP on a substrate placed on a grounded collector. This technique can be used to prepare aligned nanofibers as described herein or to produce randomly distributed nanofibers. In one aspect, the protein is laminin. In one aspect, the polymer is PCL.

In one aspect, the sheets of nanofibers are formed upon electrospinning. In one aspect, the sheets comprise one layer. In one aspect, the sheets comprise at least two layers. In another aspect, the sheets comprise at least three layers. The invention further provides for incorporating or adding additional ingredients, compounds, agents, drugs, or cells, including, but not limited to cell growth and differentiation factors, other extracellular matrix proteins, antibiotics, and antiviral agents, and combinations, derivatives, and analogs thereof.

In one aspect, laminin is dissolved at a concentration ranging from about 0.1% w/v to about 50% w/v. In one aspect, laminin is dissolved at a concentration ranging from about 0.5% to about 25% w/v. In another aspect, laminin is dissolved at a concentration ranging from about 1.0% to about 10% w/v. In yet another aspect, laminin is dissolved at a concentration ranging from about 2.0% to about 8% w/v. In a further aspect, laminin is dissolved at a concentration ranging from about 4.0% to about 6.0% w/v. In one aspect, laminin is dissolved in HFP. In one aspect, it is dissolved in TFA (trifluoroacetic acid) or in TFE (trifluoroethanol).

In one aspect, the laminin-polymer mixture is dissolved at a concentration ranging from about 1% w/v to about 50% w/v total polymer (protein+synthetic polymer) in the solvent. In one aspect, the laminin-polymer mixture is dissolved at a concentration ranging from about 2% w/v to about 25% w/v total polymer. In one aspect, the laminin-polymer mixture is dissolved at a concentration ranging from about 4% w/v to about 10% w/v total polymer. In one aspect, the laminin-polymer mixture is dissolved at a concentration ranging from about 6% w/v to about 8% w/v total polymer. In one aspect, the laminin-polymer mixture is dissolved in HFP. In one aspect, the total polymer concentration is 5%. In another aspect, the total polymer concentration is 8%. In one aspect, the polymer is PCL.

In one aspect, the total protein-polymer mixture used for electrospinning nanofibers is prepared at a weight to volume total percentage of the solution of about 1% to about 70%. In one aspect, the total protein-polymer mixture used for electrospinning nanofibers is prepared at a weight/volume total percentage of the solution of about 70%, about 50%, about 25%, about 20%, about 15%, about 10%, about 9%, about 8%, about 7%, about 6%, about 5%, about 4%, about 3%, about 2%, or about 1%. In one aspect, the weight to volume percentage of total protein-polymer mixture in HFP is 5%. In one aspect, the weight to volume percentage of total protein-polymer mixture in HFP is 8%. In one aspect, the protein is laminin. In one aspect, the polymer is a synthetic polymer. In one aspect, the synthetic polymer is PCL.

In one aspect, the concentration or amount of protein to polymer in the mixture prepared for electrospinning is from about 0.1% to about 70%, weigh to weight. In one aspect, the concentration or amount of the protein to polymer in the mixture prepared for electrospinning is about 0.1%, 0.5%, 1.0%, 5.0%, 10%, 20%, 25%, 30%, 40%, 50%, or about 70%, weight/weight (protein/polymer). In one aspect, the protein is laminin. In one aspect, the polymer is PCL. For example, a concentration of protein to polymer of 0.1% is a ratio of 1:1000, for 1.0% it would be 1:100, etc.

In one aspect, the voltage is applied at a range of about 10 kv to about 25 kv. In another aspect, the voltage is about 20 kv.

In one aspect, the laminin-polymer mixture dissolved in HFP is pumped at a flow rate of about 0.1 ml/hr to about 10.0 ml/hr. In another aspect, the flow rate is about 0.5 ml/hr to about 5.0 ml/hr. In yet another aspect, the flow rate is about 1.0 ml/hr to about 3.0 ml/hr.

In one aspect, the collector is placed at a distance of about 5.0 cm to about 30 cm from the dispensing opening. In another aspect, the distance is about 12.5 cm to about 25 cm.

In one embodiment, the substrate is surface-charged before placing on said grounded collector. In one embodiment, the substrate is selected from the group consisting of a coverslip, a single well culture plate, a multiwell culture plate, a chambered culture slide, a multi-chambered culture slide, a cup, a flask, a tube, a bottle, a perfusion chamber, a fermenter, and a bioreactor. In one aspect, the substrate is a coverslip.

In one aspect, the electrospun laminin-polymer mixture comprises nanofibers. In one aspect, a nanofiber comprises laminin and polymer. In one aspect, the nanofibers form a mesh. In one aspect, the nanofibers comprise diameters of about 10 nm to about 1,000 nm. In another aspect, the nanofibers comprise diameters of about 50 nm to about 500 nm. In yet another aspect, the nanofibers comprise diameters of about 75 nm to about 400 nm. In a further aspect, the nanofibers comprise diameters of about 100 nm to about 300 nm. In another aspect, the nanofibers comprise diameters of about 125 nm to about 250 nm.

In one aspect, the laminin is laminin I.

In another embodiment, the present invention provides a protein-polymer nanofiber structure comprising an environment for proliferation and differentiation of cells comprising one or more nanofibers and a substrate, wherein said nanofibers are prepared by electrospinning a protein and polymer mixture, further wherein said nanofibers are not crosslinked. In one aspect, the nanofibers maintain their structure when wetted by media. In one aspect, the nanofibers are aligned.

In one embodiment, the nanofiber structure is suitable for cell attachment and cell culture. In one aspect, the environment further comprises additional compounds. In one aspect, the structure comprises one or more growth factors. In one aspect the growth factors, include, but are not limited to, vascular endothelial growth factor, transforming growth factor-beta, transforming growth factor-alpha, epidermal growth factor, endothelial growth factor, platelet-derived growth factor, nerve growth factor, fibroblast growth factor, and insulin growth factor. In one aspect, the structure releases the growth factors. In another aspect, the laminin-polymer nanofiber structure comprises one or more differentiation factors.

In one embodiment, the nanofibers comprise laminin I and a polymer. Some preferred synthetic matrix materials for electrospinning with a protein include, but are not limited to the polymers poly(lactic acid) (PLA), poly (l-lactic acid) (PLLA), polyglycolic acid (PGA), copolymers of PLA and PGA, polycaprolactone (PCL), poly(ethylene-co-vinyl acetate) (EVOH), poly(vinyl acetate) (PVA), polyethylene glycol (PEG), poly(glycerol sebacate) (PGS), poly(d,l-lactic-co-glycolic acid 50:50) (PLGA5050), poly(d-l-lactic-co-glycolic acid 85:15) (PLGA8515), polydioxanone (PDO), polyphosphazenes, polyurethane (PU) and modifications, analogs, and derivatives, thereof, polyhydroxybutyrates (PHB), poly-3-hydroxybutyrate (P3HB), poly-4-hydroxybutyrate (P4HB), polyhydroxyvalerate (PHV), polyhydroxyhexanoate (PHH), polyhydroxyoctanoate (PHO), poly(3-hydroxybutyrate-co-3-hydroxyvalerate) (PHBV), and poly (ethylene oxide) (PEO), as well as co-polymers, analogs, derivatives, modifications, and mixtures thereof.

In one aspect, the polymer is PCL.

In one embodiment, the nanofibers form a mesh. Meshes may, for example, be applied directly to a site of injury. Additionally, the nanofibers may be applied to or in a substrate or vehicle and then delivered or administered. For example, a nanofiber mesh of the invention may be applied to the lumen of a conduit, which can be used when reapposing a severed nerve and the nanofibers will help stimulate axonal regeneration and healing of the injured nerve.

In one embodiment, the laminin-polymer nanofibers supports neurite extension. In one aspect, the nanofibers support neurite extension in the absence of NGF.

In one aspect, the nanofibers support proliferation and differentiation of cells selected from the group consisting of stem cells, pluripotent stem cells, committed stem cells, embryonic stem cells, adult stem cells, bone marrow stem cells, adipose stem cells, umbilical cord stem cells, dura mater stem cells, precursor cells, differentiated cells, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, normal cells, cancer cells, Schwann cells, and neurons.

The invention further provides biologically active electrospun laminin prepared by the methods described herein. In one aspect, the laminin is laminin I.

The invention also provides tissue culture containers comprising laminin-polymer nanofibers. The containers include, but are not limited to, a coverslip, a single well culture plate, a multiwell culture plate, a chambered culture slide, a multichambered culture slide, a cup, a flask, a tube, a bottle, a perfusion chamber, a fermenter, and a bioreactor.

The present invention also provides compositions and methods useful for manufacturing or preparing a tissue, scaffolding, etc. In one aspect, the method encompasses layering one or more nanofiber structures of the invention, wherein the nanofibers comprise a mixture of protein and a polymer, to form a single or multi-layered assembly comprising an environment suitable for the growth of living cells in cell culture, by depositing viable cells onto the assembly and then culturing the assembly and cells under conditions that promote growth and/or differentiation of the deposited cells. In one aspect, the cells include, but are not limited to, stem cells, pluripotent stem cells, committed stem cells, embryonic stem cells, adult stem cells, bone marrow stem cells, adipose stem cells, umbilical cord stem cells, dura mater stem cells, precursor cells, differentiated cells, osteoblasts, myoblasts, neuroblasts, neurons, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In one aspect, more than one cell type can be used.

Various aspects and embodiments of the invention are described in further detail below.

randomly oriented and (F) aligned PCL nanofibers illustrate the effectiveness of insulating gap alignment.

FIG. 6. Effects of composition and orientation on sensory and motor response. (A) All conduits containing nanofibers showed decreasing thermal withdrawal latency periods over time. Data indicates operated leg response time normalized to un-operated leg response time. No significant differences were found among un-operated legs or sham operated legs. * indicates significant difference from sham (p<0.05), + indicates significant difference from hollow. (B) Motor response was measured by changes in toe spread factor. Toe spread typically decreases with tibial nerve deficits, as evidenced by the hollow conduits. PCL random and aligned perform better than 10% laminin random; however, 10% laminin aligned shows less shift than PCL aligned, and may therefore indicate fastest return to normal toe spread. Error bars represent standard error.

FIG. 7. Electrophysiology: Nerve conduction velocity. Sample electrode traces show electrophysiological response in (A) empty conduits and (B) conduits containing nanofibers after six weeks. Direction of stimulation is indicated on the plots. No impulses were recorded in animals with empty conduits. Electrode placement for anterograde conduction was stimulating electrode proximal to injury site, recording electrode distal; placement for retrograde conduction was stimulating electrode distal to injury site, recording electrode proximal; placement for nerve to muscle conduction was stimulating electrode proximal to injury site, recording electrode in the belly of the gastrocnemius muscle. Nerve conduction velocity was calculated from latencies (ms) using the distance between electrodes (mm). (C) Forward conduction velocity indicates stimulation proximal to injury and recording distal to injury site. (D) Reverse conduction indicates stimulation distal to injury and recording proximal to injury site. Forward conduction velocity appears greater with laminin content, but data were not significant (p>0.05). Reverse conduction velocity was significantly greater when animals received conduits containing aligned nanofibers (p<0.01). All conduits containing nanofibers showed significantly greater conduction velocity in both directions than empty conduits (p<0.001).

FIG. 8. Axonal regeneration within the conduit. Representative confocal microscopy images showing immunohistochemistry for NF160, an axonal marker. (A) PCL random and (B) laminin blend random have some tissue in-growth from proximal end to midline, but the neurons tend to be more spread out and less organized than when the nanofibers are aligned. Both (C) PCL aligned and (D) laminin-PCL blend aligned show greater density of axonal staining, suggesting greater tissue regrowth. The aligned images also show greater alignment of the re-growing neurons. All images are oriented with the proximal stump toward the bottom, with re-growth occurring upward.

Figure 9:
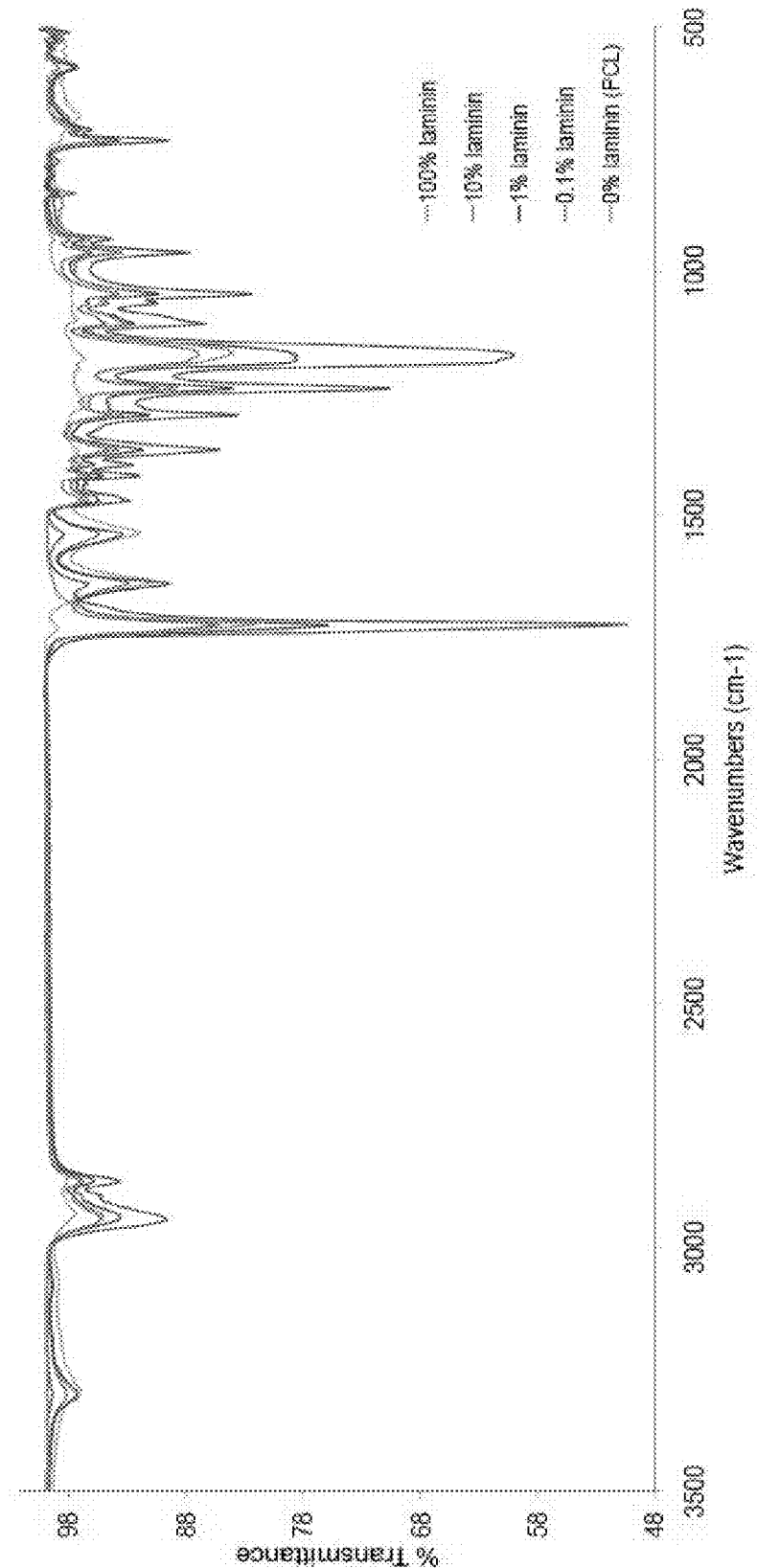

FIG. 9. Spectral analysis of electrospun nanofibers. The groups tested include, 100% laminin, 10% laminin, 1% laminin, 0.1% laminin, and 0% laminin (PCL). The ordinate represents % Transmittance and the abscissa represents Wavenumbers (cm-1)

DETAILED DESCRIPTION

Abbreviations and Acronyms
ANOVA—analysis of variance
ASC—adipose stem cell
ATR—attenuated total reflectance
DMEM—Dulbecco's modified Eagle's medium
DRG—dorsal root ganglion
DSC—dura mater stem cell
ECM—extracellular matrix
EHS—Engelbreth-Holm-Swarm
EMG—electromyography
ESC—embryonic stem cell
FFT—fast fourier transform
FTIR—fourier transform infrared spectroscopy
GPC—gel permeation chromatography
HFP—1,1,1,3,3,3-hexafluoro-2-propanol
IR—infrared
LNF—laminin nanofiber
NGF—nerve growth factor
PBS—phosphate-buffered saline
PCL—polycaprolactone
PFA—paraformaldehyde
RBM—reconstituted basement membrane
SEM—scanning electron microscope
TFA—trifluoroacetic acid
TFE—trifluoroethanol
TFI—tibial function index
THF—tetrahydrofuran
UTS—ultimate tensile strength
YFP—yellow fluorescent protein Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about", as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

The term "aligned", as used herein is meant to be interpreted in the context of its use with nanofibers and when used alone generally means that the nanofibers are aligned in parallel or in the same direction in general. The term "randomly aligned" means that the nanofibers may have any orientation within their setting (e.g., a mesh, network, or film).

As used herein, "amino acids" are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |

-continued

| Full Name | Three-Letter Code | One-Letter Code |
|---|---|---|
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

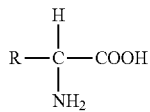

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine. As used herein, an "analog" of a chemical compound is a compound that, by way of example, resembles another in structure but is not necessarily an isomer (e.g., 5-fluorouracil is an analog of thymine).

The term "bioactive laminin", as used herein, means laminin which maintains some or all of the biological properties of laminin. The term bioactive is used interchangeably with "biologically active" and "functional". The term "biocompatible," as used herein, refers to a material that does not elicit a substantial detrimental response in the host.

The term "blend", as used herein, as well as the term "mixture", is used to indicate that the combination of, for example, laminin and PCL, is mixed before being electrospun, hence the electrospun product has the two products mixed in the nanofibers, as opposed to electrospinning laminin separately from PCL to form nanofibers which are only laminin or only PCL.

The terms "cell" and "cell line," as used herein, may be used interchangeably. All of these terms also include their progeny, which are any and all subsequent generations. It is understood that all progeny may not be identical due to deliberate or inadvertent mutations.

The terms "cell culture" and "culture," as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

The phrases "cell culture medium," "culture medium" (plural "media" in each case) and "medium formulation" refer to a nutritive solution for cultivating cells and may be used interchangeably.

A "compound," as used herein, refers to a polypeptide, an isolated nucleic acid, and to any type of substance or agent that is commonly considered a chemical, drug, or a candidate for use as a drug, as well as combinations and blends of the above.

A "conditioned medium" is one prepared by culturing a first population of cells or tissue in a medium, and then harvesting the medium. The conditioned medium (along with anything secreted into the medium by the cells) may then be used to support the growth or differentiation of a second population of cells.

The term "culture container" as used herein means a receptacle for holding media for culturing a cell or tissue. The culture container may, for example, be glass or plastic. Preferably the plastic is non-cytotoxic. The term culture container includes, but is not limited to, single and multiwell culture plates, chambered and multi-chambered culture slides, coverslips, cups, flasks, tubes, bottles, roller bottles, spinner bottles, perfusion chambers, bioreactors, and fermenters.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets, and effector activities of these cytokines have been described.

The term "delivery vehicle" refers to any kind of device or material which can be used to deliver cells in vivo or can be added to a composition comprising cells administered to an animal. This includes, but is not limited to, implantable devices, matrix materials, gels, etc.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

The term "differentiation factor" as used herein means a bioactive molecule that promotes the differentiation of cells. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors may also promote the growth of a cell or tissue. TGF and IL-3, for example, may promote differentiation and/or growth of cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

A "disease or disorder associated with aberrant osteoclast activity" refers to a disease or disorder comprising either increased or decreased: osteoclast activity; numbers of osteoclasts; or numbers of osteoclast precursors.

A "dispensing container" refers to a vessel such as a syringe, which is used in the process of electrospinning. The syringe may have a needle attached and the gauge may be varied, depending in the particular conditions needed when electrospinning "Electroaerosoling" means a process in which droplets are formed from a solution or melt by streaming a solution or melt through an orifice in response to an electric field.

"The terms "electroprocessing" and "electrodeposition" shall be defined broadly to include all methods of electrospinning, electrospraying, electroaerosoling, and electrosputtering of materials, combinations of two or more such methods, and any other method wherein materials are streamed, sprayed, sputtered, or dripped across an electric field and toward a target. The electroprocessed material can be electroprocessed from one or more grounded reservoirs in the direction of a charged substrate or from charged reservoirs toward a grounded target. The term electroprocessing is not limited to the specific examples set forth herein, and it includes any means of using an electrical field for depositing a material on a target. The material may be in the form of fibers, powder, droplets, particles, or any other form. The target may be a solid, semisolid, liquid, or any other material.

"Electrospinning" means a process in which fibers are formed from a solution or melt by streaming a solution or melt through an orifice in response to an electric field.

The term "film" as used herein refers to a two-dimensional composition or coating comprising a protein such as laminin or a polymer such as PCL, or a mixture, but the components are not in a nanofiber configuration, i.e., not prepared by electrospinning to produce nanofibers. Films are generally applied as a solution and then subjected to evaporation to remove the solvent.

A "fragment" or "segment" is a portion of an amino acid sequence, comprising at least one amino acid, or a portion of a nucleic acid sequence comprising at least one nucleotide. The terms "fragment" and "segment" are used interchangeably herein. A "biologically active fragment" of a peptide or protein is one which retains activity of the parent peptide such as binding to a natural ligand or performing the function of the protein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

"Graft" refers to any free (unattached) cell, tissue, or organ for transplantation.

"Allograft" refers to a transplanted cell, tissue, or organ derived from a different animal of the same species.

"Xenograft" refers to a transplanted cell, tissue, or organ derived from an animal of a different species.

The term "growth factor" as used herein means a bioactive molecule that promotes the proliferation of a cell or tissue. Growth factors useful in the present invention include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "ingredient" refers to any compound, whether of chemical or biological origin, that can be used in cell culture media to maintain or promote the growth or proliferation of cells. The terms "component," "nutrient" and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, means to suppress or block an activity or function such that it is lower relative to a control value. The inhibition can be via direct or indirect mechanisms. In one aspect, the activity is suppressed or blocked by at least 10% compared to a control value, more preferably by at least 25%, and even more preferably by at least 50%. The term "inhibitor" as used herein, refers to any compound or agent, the application of which results in the inhibition of a process or function of interest, including, but not limited to, differentiation and activity Inhibition can be inferred if there is a reduction in the activity or function of interest.

The term "injury" refers to any physical damage to the body caused by violence, accident, trauma, or fracture, etc.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

As used herein, the term "insult" refers to injury, disease, or contact with a substance or environmental change that results in an alteration of tissue or normal cellular metabolism in a tissue, cell, or population of cells.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The terms "nanofibrillar structure supports the proliferation and differentiation of cells" or "nanofibers structure supports the proliferation and differentiation of cells" should not be construed to mean that it must support both proliferation and differentiation of a specific cell, but should be construed in the broad sense of being able to support the proliferation and/or differentiation of many cell types. Additionally, the term does not mean that additional things such as supplements, growth factors, and differentiation factors do not need to be added when culturing a particular cell type in an effort to support its growth and/or differentiation.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions. As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "material" refers to any compound, molecule, substance, or group or combination thereof that forms any type of structure or group of structures during or after electroprocessing. Materials include natural materials, synthetic materials, or combinations thereof. Naturally occurring organic materials include any substances naturally found in the body of plants or other organisms, regardless of whether those materials have or can be produced or altered synthetically. Synthetic materials include any materials prepared through any method of artificial synthesis, processing, or manufacture. Preferably, the materials are biologically compatible materials.

The term "mesh" as used herein, refers to a collection of nanofibers, which can be one or more non-woven layers of polymer nanofibers and thus the mesh comprises what is referred to herein as a "nanofibrillar structure". Nanofibers within the mesh may be either randomly oriented or are deposited in a controlled fashion, such as aligned in parallel. Such a mesh comprises both nanofibers and "pores" (spaces not occupied by fibers). The terms "mesh" and "sheet" are used interchangeably.

The term "nanofiber" as used herein means a fiber comprising a diameter of about 1000 nanometers or less.

The term "nanofibrillar structure" as used herein means a structure comprising one or more nanofibers, wherein the structure is defined by a network or mesh of one or more nanofibers. In some embodiments, the nanofibrillar structure comprises a substrate wherein the nanofibrillar structure is defined by a network of one or more nanofibers deposited on a surface of the substrate. The nanotopography, the topography of the nanofiber network and the arrangement of the nanofibers of the nanofiber network in space, is engineered to provide an in vitro biomimetic substratum that is more tissue compatible for the promotion of homotypic or heterotypic cell growth and/or cell differentiation in single layer or multi-layered cell culture. The nanofibrillar structures may be layered to form a multi-layered nanofibrillar assembly, cellular array, or tissue structure.

The term "network" as used herein means a random or oriented distribution of nanofibers in space that is controlled to form an interconnecting net with spacing between fibers selected to promote growth and culture stability. Physical properties of the network including, but not limited to, texture, rugosity, adhesivity, porosity, solidity, elasticity, geometry, interconnectivity, surface to volume ratio, fiber diameter, fiber solubility/insolubility, hydrophilicity/hydrophobicity, fibril density, and fiber orientation may be engineered to desired parameters.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

A "recombinant polypeptide" is one which is produced upon expression of a recombinant polynucleotide.

A peptide encompasses a sequence of 2 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH2OC(O)NR—), a phosphonate linkage, a —CH2-sulfonamide (—CH2-S(O)2NR—) linkage, a urea (—NHC(O)NH—) linkage, a—CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)$_2$R group, to a —NHC(O)NHR group where R and R1 are hydrogen or C1-C4 alkyl with the proviso that R and R1 are not both hydrogen;

3. peptides wherein the C terminus is derivatized to —C(O) R2 where R 2 is selected from the group consisting of C1-C4 alkoxy, and —NR3R4 where R3 and R4 are independently selected from the group consisting of hydrogen and C1-C4 alkyl.

The term "protein-polymer", as used herein, is meant to also include peptides, not just proteins.

The term "pumping said protein-polymer mixture dissolved in HFP through an opening in said dispensing container" refers to the route in which the protein-polymer mixture is electrospun, such as through the tip of a syringe.

As used herein, the term "purified" and like terms relate to an enrichment of a cell, cell type, molecule, or compound relative to other components normally associated with the cell, cell type, molecule, or compound in a native environment. The term "purified" does not necessarily indicate that complete purity of the particular cell, cell type, molecule, or compound has been achieved during the process.

A "reversibly implantable" device is one which may be inserted (e.g. surgically or by insertion into a natural orifice of the animal) into the body of an animal and thereafter removed without great harm to the health of the animal.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

The term "stimulate" as used herein, means to induce or increase an activity or function level such that it is higher relative to a control value. The stimulation can be via direct or indirect mechanisms. In one aspect, the activity or differentiation is stimulated by at least 10% compared to a control value, more preferably by at least 25%, and even more preferably by at least 50%.

A "subject" of analysis, diagnosis, or treatment is an animal. Such animals include mammals, preferably a human.

As used herein, a "subject in need thereof" is a patient, animal, mammal or human, who will benefit from the method of this invention.

The term "substantially pure" describes a compound, e.g., a protein or polypeptide or other compound which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "substrate" as used herein means any surface on which electrospun laminin, laminin nanofibers, meshes or networks of laminin nanofibers are deposited. The substrate may be any surface that offers structural support for the deposited network or mesh of nanofibers. The substrate may comprise, for example, glass or plastic. Preferably, the plastic is non-cytotoxic. The substrate may, for example, be a film or culture container. "Substrate" should be interpreted to mean not just a surface upon which material can be deposited, but additionally the surface and the materials that have been deposited upon it.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "total polymer concentration" refers to the total amount of protein and synthetic polymer added together to form the mixture in HFP to be used for electrospinning. It is expressed as weight to volume herein.

As used herein, the term "treating" includes prophylaxis (if specifically recited) of a specific disease, disorder, or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "wound" relates to a physical tear or rupture to a tissue or cell layer. A wound may occur by any physical insult, including a surgical procedure.

Embodiments

The present invention provides compositions and methods for mimicking three dimensional scaffolding as found in vivo to better mimic how cells grow and differentiate and to aid in, inter alia, attachment and proliferation of cells, cell differentiation, wound repair, regeneration of injured tissue, etc. In one embodiment, the injured tissue is nerve tissue.

The present invention provides methodologies and parameters for fabrication of the hybrid biomaterial by blending pure laminin or complex extracts of tissues containing laminin with biopolymers such as polycaprolactone (PCL), poly-lactic/polyglycolic acid copolymer (PLGA) or Polydioxanone (PDO) in, for example, HFP, TFA, or TFE, fabrication of substrates and scaffolds and devices from the hybrid biomaterial in forms such as films, nanofibers by electrospinning or microspheres, and the biological or biomedical use of the material or devices derived from it.

Previous work prepared and used nanofibers that were homogeneous comprising one component, such as a single protein or single polymer. The present invention is based on the discovery herein that protein and polymer can be mixed together and then subjected to electrospinning to form nanofibers that are blends or mixtures (i.e., heterogeneous) of these multiple components, and that these new nanofiber mixtures unexpectedly can be prepared such that they possess the best qualities of each component and can be made much more cheaply than the present nanofibers. For example, advantages of the preparation and use of the mixtures, besides the cost savings from the reduction in the amount of pure protein such as laminin that is needed, are no diminution of biological activity (e.g., cell attachment, differentiation, neurite outgrowth), and less chance of the development of an immune response to the protein or other basement membrane components, particularly glomerular nephritis or other unwanted or unintended biological responses that can occur when protein is administered to a subject. Additionally, the advantages of using a polymer in the mixture, particularly a synthetic polymer such as PCL (which is much cheaper than purified protein), include its more consistent quality from batch to batch and better mechanical properties (easier to manipulate, can hold a suture, etc.).

The present invention further provides the preparation and use of nanofiber mixtures that have been aligned, which are disclosed as being useful for such things as stimulating directionality of healing and regrowth of injured nerves. The present invention further provides for using Cell proliferation and differentiation are regulated by unique spatial interactions between cells. Spatial cues in conjunction with the topologically distinct location of specific attachment molecules, and the release of specific humoral factors, such as growth and differentiation factors, function as signals to the cell to proliferate, differentiate, migrate, remain in a resting state, or initiate apoptosis. The capacity of the cell to respond to these signaling triggers is dependent on the availability of specific cell surface and intracellular receptors. The signal transduction pathways that are stimulated by these molecules depend on the organization and structure of the cell cytoskeleton whose architecture is a function of multipoint cell surface interactions with these signaling molecules, surrounding cells, and extracellular matrix.

When designing cell and tissue culture environments, it is important to consider the cellular interactions that must be incorporated into the growth environment. Cell types, spatial cues, and chemical triggers and modulators play a significant role in regulating gene expression within interacting cells (Li et al., 2002, FASEB J., 17:97-99; Botarro et al., 2002, Ann. N.Y. Acad. Sci., 961:143-153; Kunz-Schughart et al., 2003, Am. J. Physiol. Cell Physiol., 284:C209-C219; Cukierman et al., 2001, Science, 294:1708-1712). Past advances in the practice of cell and tissue culture have been directed toward providing the biochemical and physical conditions that approximate the complex in vivo microenvironment within a tissue (Cukierman et al., 2001, Science, 23:1708-1712; Li et al., 2002, FASEB J., 17:97-99; Chiu et al., 2000, Proc. Natl. Acad. Sci. USA, 97:2408-2413). These efforts have been limited by factors that include the use of cell lines that have been continuously grown on and selected for their ability to proliferate on planar culture surfaces that lack the spatial cues and chemical triggers and modulators present in tissue in vivo.

Another aspect of the invention is a nanofibrillar structure comprising one or more nanofibers and wherein the nanofibrillar structure is defined by a network of one or more nanofibers. In an embodiment, the nanofibers are deposited on a surface of a substrate.

In one embodiment the substrate is a conduit or a substrate applied to a conduit. In one aspect, the substrate comprises at least one polymer. In one aspect, the substrate comprises at least one protein. In one aspect, the substrate comprises at least one polymer and at least one protein.

In an embodiment, the substrate comprises glass or plastic. In a further embodiment, the substrate is a surface of a culture container.

The nanofibrillar structures may be utilized singly or layered to form a multi-layered assembly of nanofibrillar structures for cell or tissue culture.

The nanofibrillar structure of the invention has many in vivo and ex vivo uses including wound repair, growth of artificial skin, veins, arteries, tendons, ligaments, cartilage, heart valves, organ culture, treatment of burns, and bone grafts. In an embodiment, a diverse array of growth environments for a cell or tissue may be constructed by engineering specific chemical and physical properties into the nanofiber network, substrate, and/or spacers comprising the individual nanofibrillar structure elements and/or sequentially layering individual nanofibrillar structures. In certain embodiments, the unique nature of the environment can be obtained from the heterogeneous nature of the fiber diameter and composition. Physical properties and/or characteristics of the individual nanofiber, nanofibrillar structure, and nanofibrillar network including, but not limited to, texture, rugosity, adhesivity, porosity, solidity, elasticity, geometry, interconnectivity, surface to volume ratio, fiber diameter, fiber solubility/insolubility, hydrophilicity/hydrophobicity, and fibril density may be varied and/or modified to construct nano- and/or micro-environments that promote a desired cellular activity, including proliferation and/or differentiation. Specific nano- and/or micro-environments may be engineered within individual nanofibrillar structures or within a cellular array comprising two or more nanofibrillar structures.

Specific chemical properties and recognition motifs such as polypeptides, lipids, carbohydrates, amino acids, nucleotides, nucleic acids, polynucleotides, or polysaccharides including, but not limited, to growth factors, differentiation factors, fibrous proteins, adhesive proteins, glycoproteins, functional groups, adhesive compounds, deadhesive compounds, and targeting molecules may be engineered into the nanofibrillar network substrate.

The present invention is also directed to methods of manufacturing a tissue. In an embodiment, two or more nanofibrillar structures are layered to form a multi-layered nanofibrillar assembly. Viable cells are deposited on the fiber and the structure is cultured under conditions that promote growth, migration, and/or differentiation of the deposited cells. In a further embodiment, nano- and/or micro-environments that promote cellular activity may be engineered within an individual matrix by varying and/or modifying selected physical and/or chemical properties of the growth matrix.

In another embodiment, multiple cell types are cultured on individual nanofibrillar structures under different culture conditions. Two or more of the individual nanofibrillar structures are then layered to form a multi-layered nanofibrillar assembly and the assembly is cultured under conditions that promote a desired cellular activity, including growth and/or differentiation of the cells. In a further embodiment, nano- and/or micro-environments that promote cellular activity may be engineered within an individual nanofibrillar structure by varying and/or modifying selected physical and/or chemical properties of the nanofibrillar structure or within the nanofibrillar assembly by selectively layering the individual nanofibrillar structures to obtain the desired nano- or microenvironment. Homogeneous or heterogeneous fiber diameters and compositions may be selected to optimize proliferation and/or differentiation.

The compositions and nanofibrillar structures of the present invention comprise electrospun nanofibers prepared by mixing a protein and a polymer and subjecting the mixture to electrospinning. In one aspect, the protein is laminin. The electrospun laminin can constitute or be formed, for example, from natural laminin, genetically engineered laminin, or laminin modified by conservative amino acid substitutions, non-conservative amino acid substitutions or substitutions with non-naturally occurring amino acids. The laminin used in electrospinning can be derived from a natural source, manufactured synthetically, or produced through any other means. Numerous methods for producing laminins and other proteins are known in the art. Synthetic laminin can be prepared to contain specific desired amino acid sequences. The polymer can be a synthetic polymer.

Some preferred synthetic matrix materials for electrospinning with a protein include, but are not limited to, polymers such as poly(lactic acid) (PLA), poly (l-lactic acid) (PLLA), polyglycolic acid (PGA), copolymers of PLA and PGA, polycaprolactone, poly(ethylene-co-vinyl acetate), (EVOH), poly (vinyl acetate) (PVA), polyethylene glycol (PEG), poly(glycerol sebacate) (PGS), poly(d,l-lactic-co-glycolic acid 50:50) (PLGA5050), poly(d-l-lactic-co-glycolic acid 85:15) (PLGA8515), polydioxanone (PDO), polyphosphazenes, polyurethane (PU) and modifications, analogs, and derivatives, thereof, polyhydroxybutyrates (PHB), poly-3-hydroxybutyrate (P3HB), poly-4-hydroxybutyrate (P4HB), polyhydroxyvalerate (PHV), polyhydrorxyhexanoate (PHH), polyhydroxyoctanoate (PHO), poly(3-hydroxybutyrate-co-3-hydroxyvalerate) (PHBV), and poly(ethylene oxide) (PEO), as well as co-polymers, analogs, derivatives, modifications, and mixtures thereof.

One class of polymers currently on the market are the polyesters, such as poly(lactic-co-glycolic) acid (PLGA), that has been FDA approved for use as suture and pin fixation devices for fractures.

Another novel polymer that has received great attention as a biomaterial is the inorganic polyphosphazenes. Previously it was demonstrated that polyphosphazenes are a suitable biodegradable polymer to support the repair of bone in vitro. These polymers can be fashioned into three-dimensional matrices that attempt to simulate the physico-chemical and mechanical properties of tissue. Polyphosphazenes are high molecular weight polymers with an inorganic backbone consisting of nitrogen and phosphorous atoms linked by alternating single and double bonds. Starting with the macromolecular intermediate poly(dichlorophosphazene), a number of different molecules can be formed by nucleophilic substitution of the chlorine atoms with various organic side groups. This process allows polymers to be synthesized which express different physical, chemical, and mechanical properties depending on which side groups are attached to the phosphorus atoms. Upon degradation, molecules such as phosphate, ammonia, and amino acids are released. These molecules have been observed to be non-toxic to animal tissue and may even cause cell adhesion and growth, thus promoting their potential use as a biocompatible scaffolding to support the development of new tissue.

Polyphosphazenes are high molecular weight biodegradable polymers with an inorganic backbone consisting of alternate nitrogen and phosphorus atoms with each phosphorus atom is attached to two organic side groups, having a general structure as shown in Formula I.

Polyphosphazenes are biocompatible, biodegradable, and the rate of their degradation can be modulated by changing the side groups attached to the phosphorus atom. Polyphosphazenes degrade in the body into products that are non-toxic and easily disposed of by the body. Such degradation products include phosphates, ammonia, alcohol, and the corresponding side chains. Because of their degradation properties, polyphosphazenes have been used as drug delivery vehicles.

Various polyphosphazene compounds are contemplated for use in the composites of the present invention. In one embodiment, the polyphosphazene contained in the composites of the invention is poly[(50% ethyl alanato)(50% phenylphenoxy)phosphazene] as shown in Formula II.

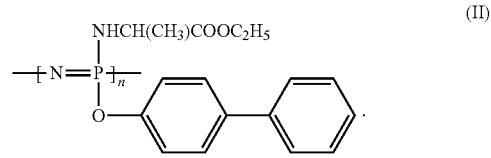

Other preferred polyphosphazene compounds for use in the composites of the present invention include:

Poly[bis(ethyl alanato) phosphazene] as shown in Formula III;

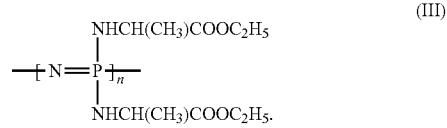

Poly[(50% ethyl alanato) (50% ethyl glycinato) phosphazene] as shown in Formula IV; and

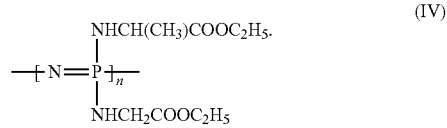

Poly[(50% ethyl alanato) (50% methyl phenoxy)phosphazene] as shown in Formula V.

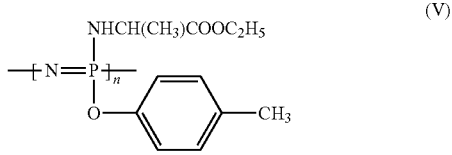

(V)

It is also contemplated that other polyphosphazene compounds can be used in compositions of the present invention, including the polyphosphazenes described in U.S. Pat. No. 6,235,061, which is hereby incorporated by reference herein.

The polyphosphazenes of the present invention may be synthesized by various methods known in the art.

In some embodiments, the compositions and structures of the present invention includes additional electrospun materials. Other electrospun materials can include natural materials, synthetic materials, or combinations thereof. Some preferred examples of natural materials include, but are not limited to, amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans.

In many desirable embodiments, the electrospun protein-polymer mixture is combined with one or more additional substances. In one aspect, the protein is laminin. In one aspect, the polymer is PCL. Such substances include any type of molecule, cell, or object or combinations thereof. The electrospun protein-polymer mixture compositions of the present invention can further comprise one substance or any combination of substances. Several especially desirable embodiments include the use of cells as a substance combined with the protein-polymer mixture nanofiber matrix. Any cell can be used. Cells that can be used include, but are not limited to, stem cells, committed stem cells, and differentiated cells. Molecules can be present in any phase or form and combinations of molecules can be used.

Examples of desirable classes of molecules that can be used include human or veterinary therapeutics, cosmetics, nutraceuticals, agriculturals such as herbicides, pesticides and fertilizers, vitamins, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, plasticizers, minerals, ions, electrically and magnetically reactive materials, light sensitive materials, anti-oxidants, molecules that can be metabolized as a source of cellular energy, antigens, and any molecules that can cause a cellular or physiological response. Examples of objects include, but are not limited to, cell fragments, cell debris, organelles and other cell components, extracellular matrix constituents, tablets, and viruses, as well as vesicles, liposomes, capsules, nanoparticles, and other structures that serve as an enclosure for molecules. Magnetically or electrically reactive materials are also examples of substances that are optionally included within compositions of the present invention. Examples of electrically active materials include, but are not limited to, carbon black or graphite, carbon nanotubes, and various dispersions of electrically conducting polymers. Examples of magnetically active materials include, but are not limited to, ferrofluids (colloidal suspensions of magnetic particles).

By selecting different materials for combining with electrospun protein-polymer mixtures, or combinations thereof, many characteristics of the electroprocessed material can be manipulated. For example, the properties of a matrix, mesh, or film comprised of an electrospun protein-polymer mixture may be adjusted. Electrospun protein-polymer mixtures and other electroprocessed materials can provide a therapeutic effect when applied. In addition, selection of matrix materials can affect the permanency of an implanted matrix or conduit. Use of matrices made of natural materials such as proteins also minimize rejection or immunological response to an implanted matrix. Accordingly, selection of materials for electroprocessing and use in substance delivery is influenced by the desired use. In one embodiment, a skin patch of an electrospun protein-polymer mixture combined with healing promoters, analgesics and or anesthetics and anti-rejection substances may be applied to the skin and may subsequently dissolve into the skin. In another embodiment, an electrospun protein-polymer mixture implant for delivery to bone may be constructed of materials useful for promoting bone growth, osteoblasts, and hydroxyapatite, and may be designed to endure for a prolonged period of time. In embodiments in which the protein-polymer mixture nanofibers contain substances that are to be released, incorporating electroprocessed synthetic components, such as biocompatible substances, can modulate the release of substances from an electroprocessed composition. The protein-polymer mixture nanofibers comprising these components can be applied to a conduit. For example, layered or laminate structures can be used to control the substance release profile. Layered structures composed of alternating electroprocessed materials can be prepared by sequentially electroprocessing different materials onto a target. The outer layers are, for example, tailored to dissolve faster or slower than the inner layers.

In one aspect, the nanofibers of the unlayered structures are aligned. Unlayered structures can also be used, in which case the release is controlled by the relative stability of each component of the construct.

Multiple agents can be delivered by this method, optionally at different release rates. Layers can be tailored to provide a complex, multi-kinetic release profile of a single agent over time. Using combinations of the foregoing provides for release of multiple substances released, each with a complex profile.

In some embodiments, the electrospun protein-polymer mixture is combined with one or more substances or compounds. In embodiments in which the electrospun protein-polymer mixture compositions of the present invention comprise one or more substances, substances can include any type or size of molecules, cells, objects, or combinations thereof. The compositions of the present invention may comprise one substance or any combination of substances.

One embodiment includes cells as a substance combined with the electrospun protein-polymer mixture after electrospinning of the protein-polymer mixture. Any cell type can be used. Some preferred examples include, but are not limited to, stem cells, committed stem cells, and differentiated cells. Examples of stem cells include, but are not limited to, embryonic stem cells, bone marrow stem cells, adipose stem cells, and umbilical cord stem cells. Other examples of cells include, but are not limited to, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In some embodiments, it is unnecessary to pre-select the type of stem cell that is to be used, because many types of stem cells can be induced to differentiate in an organ specific pattern once delivered to a given organ.

Embodiments in which the substance comprises cells include cells that can be cultured in vitro, derived from a natural source, genetically engineered, or produced by any other means. Any natural source of prokaryotic or eukaryotic cells may be used. Embodiments in which the matrix is implanted in an organism can use cells from the recipient, cells from a conspecific donor or a donor from a different species, or bacteria or microbial cells. Cells harvested from a source and cultured prior to use are included.

Some embodiments use cells that have been genetically engineered. The engineering involves programming the cell to express one or more genes, repressing the expression of one or more genes, or both. One example of genetically engineered cells useful in the present invention is a genetically engineered cell that makes and secretes one or more desired molecules. When electrospun protein-polymer nanofiber matrices comprising genetically engineered cells are implanted in an organism, the molecules produced can produce a local effect or a systemic effect, and can include the molecules identified above as possible substances. Cells can also produce antigenic materials in embodiments in which one of the purposes of the matrix is to produce an immune response. Cells may produce substances to aid in the following non-inclusive list of purposes inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace neurons, skin, synovial fluid, tendons, cartilage (including, but not limited to articular cartilage), ligaments, bone, muscle, organs, dura, blood vessels, bone marrow, and extracellular matrix.

In many embodiments, cells in an electrospun matrix exhibit characteristics and functions typical of such cells in vivo.

In embodiments in which the substances or compounds are molecules, any molecule can be used. Molecules may, for example, be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules.

Several preferred embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Other preferred embodiments involve the use of growth factors, including more than one growth factor, as described herein.

In one embodiment, an effective amount of at least one growth factor, cytokine, hormone, or extracellular matrix compound or protein useful for enhancing wound healing or cell attachment, growth, differentiation or migration is administered as part of the composition. In one aspect, a combination of these agents is used or they are included in the mixture of the invention. In one aspect, growth factors useful in the practice of the invention include, but are not limited to, EGF, PDGF, GCSF, IL6, IL8, IL10, MCP1, MCP2, Tissue Factor, FGFb, KGF, VEGF, PDGF, MMP1, MMP9, TIMP1, TIMP2, TGFβ, interferons, and HGF. One of ordinary skill in the art will appreciate that the choice of growth factor, cytokine, hormone, or extracellular matrix protein used will vary depending on criteria such as the type of injury, disease, or disorder being treated, the age, health, sex, and weight of the subject, etc. In one aspect, the growth factors, cytokines, hormones, and extracellular matrix compounds and proteins are human.

Proteins and other biologically active compounds that can be incorporated into, or included as an additive within, a composition comprising compounds of the present invention include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, skeletal growth factor, enzymes, or combinations and biologically active fragments thereof. Adjuvants that diminish an immune response can also be used in conjunction with the composite of the subject invention.

Other molecules useful as compounds or substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

Embodiments involving amino acids, peptides, polypeptides, and proteins may include any type of such molecules of any size and complexity as well as combinations of such molecules. Examples include, but are not limited to, structural proteins, enzymes, and peptide hormones. These compounds can serve a variety of functions. In some embodiments, the matrix may contain peptides containing a sequence that suppresses enzyme activity through competition for the active site. In other applications, antigenic agents that promote an immune response and invoke immunity can be incorporated into a construct.

For substances such as nucleic acids, any nucleic acid can be present. Examples include, but are not limited to deoxyribonucleic acid (DNA), ent-DNA, oligonucleotides, aptamers, and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the electroprocessed matrix. The nucleic acids can be in any form that is effective to enhance uptake into cells.

Substances or compounds in the electrospun laminin compositions of the present invention also comprise objects. Examples of objects include, but are not limited to, cell fragments, cell debris, organelles and other cell components, tablets, and viruses as well as vesicles, liposomes, capsules, nanoparticles, and other structures that serve as an enclosure for molecules. In some embodiments, the objects constitute vesicles, liposomes, capsules, or other enclosures that contain compounds that are released at a time after electroprocessing, such as at the time of implantation or upon later stimulation or interaction. In one illustrative embodiment, transfection agents such as liposomes contain desired nucleotide sequences to be incorporated into cells that are located in or on the electroprocessed material or mesh. In other embodiments, cell fragments, specific cell fractions or cell debris are incorporated into the mesh. The presence of cell fragments is known to promote healing in some tissues.

Compounds and substances that can provide favorable matrix or mesh characteristics also include drugs and other substances that can produce a therapeutic or other physiological effect on cells and tissues within or surrounding an implant. Any substance may be used. In some embodiments, substances are included in the electrospun matrix that will improve the performance of the implanted electrospun matrix. Examples of substances that can be used include but are not limited to peptide growth factors, antibiotics, and/or anti-rejection drugs. Chemicals that affect cell function, such as oligonucleotides, promoters or inhibitors of cell adhesion, hormones, and growth factor are additional examples of substances that can be incorporated into the electroprocessed collagen material and the release of those substances from the electroprocessed material can provide a means of controlling expression or other functions of cells in the electroprocessed material. Alternatively, cells that are engineered to manufacture desired compounds can be included. The entire construct is, for example, cultured in a bioreactor or conventional culture or placed directly in vivo. For example, neovascularization can be stimulated by angiogenic and growth-promoting factors, administered, as peptides, proteins or as gene therapy.

Angiogenic agents can be incorporated into the electroprocessed collagen matrix. Alternatively, where neovascularization is not desired, antiangiogenic materials, such as angiostatin, may be included in the electroprocessed collagen matrix. Nerve growth factors can be electrospun into the electrospun laminin matrix to promote growth of neurons into the matrix and tissue. In a degradable electrospun laminin matrix, the gradual degradation/breakdown of the matrix will release these factors and accelerate growth of desired tissues. Substances can be incorporated into the electrospun laminin matrix to regulate differentiation of cells in the matrix. Oligonucleotides and peptides drugs such as retinoic acid are examples of such compounds and substances. Oligonucleotide DNA or messenger RNA sequences coding for specific proteins in the sense and antisense direction can also be used. For example, where expression of a protein is desired, sense oligonucleotides can be provided for uptake by cells and expression. Antisense oligonucleotides can be released, for example, to suppress the expression gene sequences of interest. Implants can be designed such that the substances affect cells contained within the matrix, outside the matrix or both.

Several methods exist for studying and quantifying specific characteristics of the matrix materials of the present invention.

The present invention also includes methods of making the compositions of the present invention. The methods of making the compositions include, but are not limited to, electrospinning laminin, and optionally electroprocessing other materials, substances or both. In the most fundamental sense, the electroprocessing apparatus for electroprocessing material includes an electrodepositing mechanism and a target. The present invention allows forming matrices that have a predetermined shape.

In a preferred embodiment, the electrospun materials form a matrix. The term "matrix" refers to any structure comprised of electroprocessed materials. Matrices are comprised of fibers, or droplets of materials, or blends of fibers and droplets of any size or shape. Matrices are single structures or groups of structures and can be formed through one or more electroprocessing methods using one or more materials. Matrices are engineered to possess specific porosities. Substances can be deposited within, or anchored to or placed on matrices. Cells are substances which can be deposited within or on matrices.

It will be appreciated by one of ordinary that some substances can be added to the protein-polymer mixture before electrospinning, but that others must be applied or added after the mixture has been electrospun.

Any solvent can be used that allows delivery of the material or substance to the orifice, tip of a syringe, or other site from which the material will be electrospun. In one aspect, the electrospun material must maintain an activity as indicated. In one aspect, an appropriate solvent for laminin is HFP. The solvent may be used for dissolving or suspending the material or the substance to be electroprocessed. Solvents useful for dissolving or suspending a material or a substance depend on the material or substance. Electrospinning techniques often require more specific solvent conditions.

One of ordinary skill in the art recognizes that changes in the concentration of materials or substances in the solutions requires modification of the specific voltages to obtain the formation and streaming of droplets from the tip of a pipette or device being used.

The electrospinning process can be manipulated to meet the specific requirements for any given application of the electrospun compositions made with these methods.

In the electrospinning process, the stream or streams can branch out to form fibers. The degree of branching can be varied by many factors including, but not limited to, voltage, ground geometry, distance from micropipette tip (such as a needle or syringe) to the collector surface, diameter of micropipette tip, and concentration of materials or compounds that will form the electroprocessed materials. This process can be varied by many factors including, but not limited to, voltage (for example ranging from about 0 to 30,000 volts), distance from micropipette tip to the substrate (for example from 0-40 cm), the relative position of the micropipette tip and target (i.e. above, below, aside etc.), and the diameter of micropipette tip (approximately 0-2 mm).

The geometry of the grounded target can be modified to produce a desired matrix. By varying the ground geometry, for instance having a planar or linear or multiple points ground, the direction of the streaming materials can be varied and customized to a particular application.

In many embodiments, the compounds or substances comprise cells. Cells can be combined with an electrospun protein-polymer mixture by any of the means noted above for combining small objects in a matrix. Cells can, for example, be suspended in a solution or other liquid that contains the laminin, disposed in the area between the solutions and target, or delivered to a target or substrate from a separate source before, during, or after electroprocessing. Cells can be dripped through the matrix, onto the matrix as it deposits on the target, or suspended within an aerosol as a delivery system for the cells to the electrospun material. The cells can be delivered in this manner while the matrix is being formed.

The compositions and substances of the invention are also useful for preparing engineered tissue. Once the electroengineered tissue containing electrospun laminin and cells is assembled, the tissue can be inserted into a recipient. Alternatively, the structure can be placed into a culture to enhance the cell growth. Different types of nutrients and growth factors can be added to a culture (or administered to a recipient) in order to promote a specific type of growth of the engineered tissue.

Electrospun protein-polymer mixture materials, such as matrices and meshes, are useful in the formation of prostheses. One application of the electrospun laminin matrices is in the formation of medium and small diameter vascular prostheses. An example of a small diameter prosthesis is one having an inner diameter less than six millimeters, for example, a diameter of four millimeters. Some useful materials for this embodiment are collagen and elastin, especially collagen type I and collagen type III. Some examples include, but are not limited to coronary vessels for bypass or graft, femoral artery, popliteal artery, brachial artery, tibial artery, radial artery, arterial bifurcation, or corresponding veins. The electroprocessed material is useful, especially when combined with endothelial cells on the inside of the vascular prosthesis, and smooth muscle cells, for example a collagen tube, and also when combined with fibroblasts on the outside of the collagen tube.

Combinations of electrospun protein-polymer mixtures and other fibers, can provide optimal growth conditions for cells. In some cases, large diameter fibers can be used to form a basic structural matrix that lends mechanical support to the electrospun protein-polymer mixture construct, and the electroprocessed matrix is used as a scaffolding to deliver and/or support the cells. This facilitates cell attachment onto the structural matrix.

Preparation of conduits and applications of protein-polymer nanofiber sheets to conduits are described in Example 3.

Tissue containing electrospun protein-polymer mixtures, and optionally other material, can be engineered with an endogenous vascular system. This vascular system can be composed of artificial vessels or blood vessels excised from a donor site on the transplant recipient. The engineered tissue containing electrospun protein-polymer mixture material is then assembled around the vessel. By enveloping such a vessel with the tissue during or after assembly of the engineered tissue, the engineered tissue has a vessel that can be attached to the vascular system of the recipient.

In some embodiments, the stem cells or other cells used to construct the implant are isolated from the subject, or other compatible donor requiring tissue reconstruction. This provides the advantage of using cells that will not induce an immune response, because they originated with the subject (autologous tissue) requiring the reconstruction. Relatively small biopsies can be used to obtain a sufficient number of cells to construct the implant. This minimizes functional deficits and damage to endogenous tissues that serve as the donor site for the cells.

The electrospun protein-polymer mixture compositions of the present invention have a broad array of potential uses. Uses include, but are not limited to, manufacture of engineered tissue and organs, including structures such as patches or plugs of tissues or matrix material, prosthetics, and other implants, tissue scaffolding, repair or dressing of wounds, hemostatic devices, devices for use in tissue repair and support such as sutures, surgical and orthopedic screws, and surgical and orthopedic plates, natural coatings or components for synthetic implants, cosmetic implants and supports, repair or structural support for organs or tissues, substance delivery, bioengineering platforms, platforms for testing the effect of substances upon cells, cell culture, and numerous other uses. This discussion of possible uses is not intended to be exhaustive and many other embodiments exist.

The ability to combine cells in an electrospun protein-polymer mixture material provides the ability to use the compositions of the present invention to build tissue, organs, or organ-like tissue. Cells included in such tissues or organs can include cells that serve a function of delivering a substance, seeded cells that will provide the beginnings of replacement tissue, or both. Many types of cells can be used to create tissue or organs. Stem cells, committed stem cells, and/or differentiated cells are used in various embodiments.

The electrospun protein-polymer mixture structures and matrices of the present invention also permit the in vitro culturing of cells for study. The ability to mimic extracellular matrix and tissue conditions in vitro provides a new platform for study and manipulation of cells. In some embodiments, selected cells are grown in the matrix and exposed to selected drugs, substances, or treatments. For example, neurite extension can be studied.

Another use of electrospun protein-polymer mixtures is as a bioengineering platform for manipulation of cells in vitro. This provides for placement of cells in a matrix and treating the cells to engineer them a specific way. For example, stem cells can be placed in a matrix under conditions that will control their differentiation. Differentiation is controlled through the use of matrix materials or substances in the matrix that will influence differentiation. For example, agents, such as retinoic acid, that play a role in promoting differentiation might be placed within the matrix.

One use of the electrospun protein-polymer mixtures of the present invention is the delivery of one or more substances to a desired location. In some embodiments, the electroprocessed materials are used simply to deliver the materials. In other embodiments, the electroprocessed materials are used to deliver substances that are contained in the electroprocessed materials or that are produced or released by substances contained in the electroprocessed materials. For example, an electroprocessed material containing cells can be implanted in a body and used to deliver molecules produced by the cells after implantation. The present compositions can be used to deliver substances to an in vivo location, an in vitro location, or other locations. The present compositions can be administered to these locations using any method. In some embodiments, electrospun protein-polymer mixtures used in tissue scaffolding deliver substances that will aid in the function of the scaffolding. Any substance that will aid in the function of the scaffold may be used.

The proteins and peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride, or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, depending on the size of the peptide, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2—S—CH2), dimethylene-sulfoxide (—CH2—SO—CH2), dimethylene-sulfone (—CH2—SO2—CH2), 2'—O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic: acids can be purified by reverse phase or ion exchange HPLC, size exclusion chromatography or gel electrophoresis. Of course, the skilled artisan will recognize that the method of purification will depend in part on the size of the DNA to be purified.

The term nucleic acid also specifically includes nucleic acids composed of bases other than the five biologically occurring bases (adenine, guanine, thymine, cytosine and uracil).

Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day. Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a mammal for treatment of the diseases disclosed herein are now described.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc. Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may also be prepared, packaged, or sold in a formulation suitable for rectal administration, vaginal administration, nasal, pulmonary, and parenteral administration. Nasal and pulmonary administration may be accomplished by means such as aerosols.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self propelling solvent/powder dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein. A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1/1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically, dosages of the compound of the invention which may be administered to an animal, preferably a human, range in amount from 1 µg to about 100 g per kilogram of body weight of the subject. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, etc.

The invention also includes a kit comprising a compound or materials of the invention and an instructional material which describes administering the composition to a cell or a tissue of a subject, or the preparation of a structure described herein.

Other techniques useful for the practice of the present invention can be found in PCT Publication WO 03/099230, U.S. Pat. Publications 2007/0225631 (Bowlin et al.), 2007/0275458 (Gouma), 2007/0269481 (Li et al.), 2004/0058887 (Bowlin et al.), 2002/0042128 (Bowlin et al.), 2005/0095695 (Shindler), 2002/0094514 (Bowlin et al.), 2002/0081732 (Bowlin et al.), 2008/0038352 (Simpson et al.), Ma et al., 2005, Tissue Engineering, 11:101, and Stegemann et al., 2007, Tissue Engineering, 13:2601.

Without further description, it is believed that one of ordinary skill in the art can, using the preceding description and the following illustrative examples, make and utilize the compounds of the present invention and practice the claimed methods.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

Please note that Examples 1 and 2 are summaries of Examples 1 and 2 of U.S. patent application Ser. No. 12/598,776, from which the present application claims priority as a CIP.

Example 1

Materials and Methods—

The solvent, 1,1,1,3,3,3-hexafluoro-2-propanol (HFP) was purchased from Sigma (St Louis, Mo.). All cell culture reagents were purchased from Fisher Scientific (Pittsburgh, Pa.).

Laminin Isolation

Laminin I was purified from the EHS tumor according to previously established methods. The final laminin solution was subjected to 2 rounds of precipitation with 45% ammonium sulfate to remove most growth factors present. Purity of laminin was evaluated by SDS-PAGE and Western analysis with affinity purified antibodies to type IV collagen, entactin/nidogen and perlecan, the major contaminants of such preparations. Purity was determined to be greater than 99% laminin (w/v). Laminin was stored at −80° C.

Laminin Electrospinning

For the parametric study, a series of process parameters was chosen within ranges shown to be successful in creating submicron or nanoscale fibers of other ECM proteins such as collagens [13] and fibrinogen. Laminin was dialyzed exhaustively against $dH_2O$, lyophilized and dissolved overnight with stirring at 4° C. in HFP to achieve desired concentrations prior to electrospinning: 3, 5, or 8% (w/v) final solution. The laminin solution was loaded into a 5 mL glass syringe with an 18G blunt needle, and mounted into an Aladdin programmable syringe pump (World Precision Instruments, Sarasota, Fla.). A collector plate covered with aluminum foil was placed 12.5 or 25 cm below the tip of the needle and electrically grounded. A high voltage power supply (Gamma, Ormond Beach, Fla.) was connected with the positive lead on the needle and set at 20 kV. The syringe pump was programmed to dispense the solution at 0.5, 1.5, 2.0, or 3.0 mL/hr. Laminin was allowed to collect on the aluminum foil for at least 20 minutes before the sample was removed and the parameters changed. Samples were cut from the aluminum foil, mounted on aluminum stubs (Electron Microscopy Sciences), sputter coated with gold using a BAL-TEC SCD005 sputter coater, and imaged using a JEOL 6400 Scanning Electron Microscope (SEM) with Orion image processing at 15 kV accelerating voltage and 39 mm working distance. For comparison purposes, collagen type I isolated from rat tail tendon was dissolved at 8% (w/v) concentration in HFP and electrospun using 20 kV driving voltage, 10 cm working distance, and 1.0 mL/hr flow rate.

Fiber Diameter and Bead Area Density Analysis

Scanning electron micrographs taken on a JEOL 6400 Scanning Electron Microscope with Orion image processing were analyzed for fiber diameter using Image J (open source program available from NIH). For fiber diameter measurements, protocols previously described were followed. Briefly, images were opened in Image J and the measure tool was used to find the average diameter of at least 50 fibers per sample, with at least four samples per condition. Bead area density was determined by finding the average diameter of each bead and calculating the area based on the assumption that all beads were roughly circular in shape. The threshold function in Image J was used to change the image to black and white pixels and the total surface area of laminin was measured, including fibers and beads. This total area divided by the bead area already calculated yielded the bead area density per sample. Each bead with a diameter larger than twice the average fiber diameter was counted in each sample, and at least four sample images were used per condition. For both fiber diameter and bead area density a minimum of three samples were used with a minimum of 50 measurements made per sample, and error bars indicate standard error.

Laminin Scaffold and Film Preparation for Cell Culture

To prepare laminin nanofiber scaffolds for cell culture, 12 mm diameter round coverslip glass was surface-charged using the Lectro-Treat 3-D Surface Treater (Lectro Engineering Co., St. Louis, Mo.) and placed on the grounded collector opposite the syringe tip. Laminin was electrospun at 5% (w/v) in HFP, 12.5 cm collecting distance, 1.5 mL/hr flow rate, and 20 kV driving voltage. After laminin collected on the coverslips, the samples were removed from the collector and were sterilized under UVC radiation for 20 minutes. Coverslips were placed into wells in a 24-well plate for cell culture.

Laminin I films for cell culture were prepared on coverslips identical to those used for nanofiber scaffold preparation as previously described. Briefly, soluble laminin stock solution (sterile laminin, 3 mg/ml in tris buffered saline—0.15 M Tris, 0.05 M NaCl pH 7.5) was diluted into either distilled water or 0.1 M ammonium carbonate pH 7.8 to a final concentration of 10 μg/mL. 20 μL of the solution was evaporated overnight onto a sterile, glass coverslip 5 mm in diameter under a laminar flow hood, yielding 0.2 μg of dried laminin film covering the upper surface of each coverslip. Coverslips were then placed into wells in a 24-well plate for cell culture.

Hydration Study

LNF meshes were electrospun onto coverslips as described above. Meshes were placed in 24 well plate dishes and immersed in 500 μL DMEM plus antibiotics to maintain similarity to ASC and PC12 culture conditions. Meshes were incubated at 37° C. for 30 min, 6 hours, or 24 hours. At each time point, a group of three LNF meshes were removed from incubation, aspirated, and dried in vacuum desiccators overnight. Dried samples were mounted on aluminum mounts with carbon stickers, coated with gold, and imaged using a JEOL 6400 Scanning Electron Microscope with Orion image processing. Fiber diameters were measured as described above.

Cell Isolation and Culture

Adipose tissue was obtained through the Department of Plastic Surgery at the University of Virginia in compliance with the UVa Human Investigation Committee. ASCs were isolated from the lipoaspirate using previously described methods. Cells were grown in culture medium containing of DMEM, 10% FBS, and 1% antibiotic/antimycotic. The cells were initially plated (p=0) and maintained at 37° C. with 5% $CO_2$. Sub-confluent cells were released with 0.5% trypsin/EDTA and then either re-plated at 2000 cells/$cm^2$ or used for experiments. For serum-free culture, DMEM plus 1% antibiotic/antimycotic was used.

Cell Attachment Assay

ASC attachment was compared on laminin nanofibers and laminin films. ASCs were chosen as a promising source for nerve tissue engineering applications. Cells were dispersed using trypsin and the reaction was stopped with soybean trypsin inhibitor. After counting, cells were plated in triplicate using an initial seeding density of $1.24 \times 10^7$ cells/$cm^2$ (15000 cells per coverslip) onto coverslips coated with either laminin films or nanofibers. Substrates were placed in the incubator (37° C., 5% $CO_2$) and cells were allowed to attach for 15, 30, 60, or 120 minutes in serum free DMEM, after which time they were washed from the substrates using Hank's buffer and fixed using 4% paraformaldehyde. Serum-free medium was used to prevent serum proteins from enhancing attachment, requiring cells to utilize the laminin substrate or secrete their own matrix proteins in response to the substrate. Substrates were imaged on a Hoffman Optics inverted light microscope at 4× and cells were counted in Image J. Some ASCs were maintained in culture conditions for 3 days and then analyzed by scanning electron microscopy.

Neurite Extension Assay

A neurite extension assay was performed using PC12 cells, a cell type known to extend neurites in response to nerve growth factor (NGF) stimulation. Cells were seeded on laminin nanofiber substrates subconfluently at a density of $2.5 \times 10^4$ cells/cm$^2$ to allow sufficient space for process formation. Serum-free medium was used to prevent serum proteins from enhancing neurite extension and to illustrate the effect of the substrate specifically on neurite extension. NGF was added up to 50 ng/mL to the NGF stimulated group after two hours. Half the media was changed for each sample after 48 hours. After five days in culture, cells were rinsed in phosphate buffer solution (PBS) and then fixed in 4% paraformaldehyde for 120 minutes at 4° C. Following fixation, cells were imaged using a Nikon TE 2000-E2 confocal microscope. Representative images were acquired using a 60×/1.45 Nikon oil immersion objective and MicroFire Picture Frame imaging software (Optronics, Galeta, Calif.). Processes were established to be any cellular extension longer than the diameter of the cell; these were counted to determine number per cell.

Statistics

To compare nanofiber hydrated diameters, a one-way ANOVA was performed with a Tukey's post hoc test using Minitab software. For the cell attachment assay and neurite extension assay, cell or neurite counts were input into Minitab software and paired Student's t-tests were performed to determine statistically significant differences between conditions. Significance was asserted as $p<0.05$. Histograms were plotted in Minitab for neurite extension comparisons.

Results—

Parametric Analysis

A parametric study was necessary to determine the effects of the physical parameters of electrospinning, specifically concentration, distance, and flow rate, on resultant laminin fiber morphology. In order to create a map of parameters needed to produce particular fiber morphologies, we chose the parameters within standard ranges for biological polymer electrospinning as shown in Table 1 of U.S. application Ser. No. 12/598,776 and performed trials with each of the parameter sets. Driving voltage was held constant throughout at 20 kV. Representative scanning electron micrographs are shown in FIG. 1 of U.S. application Ser. No. 12/598,776.

Figure 6A:
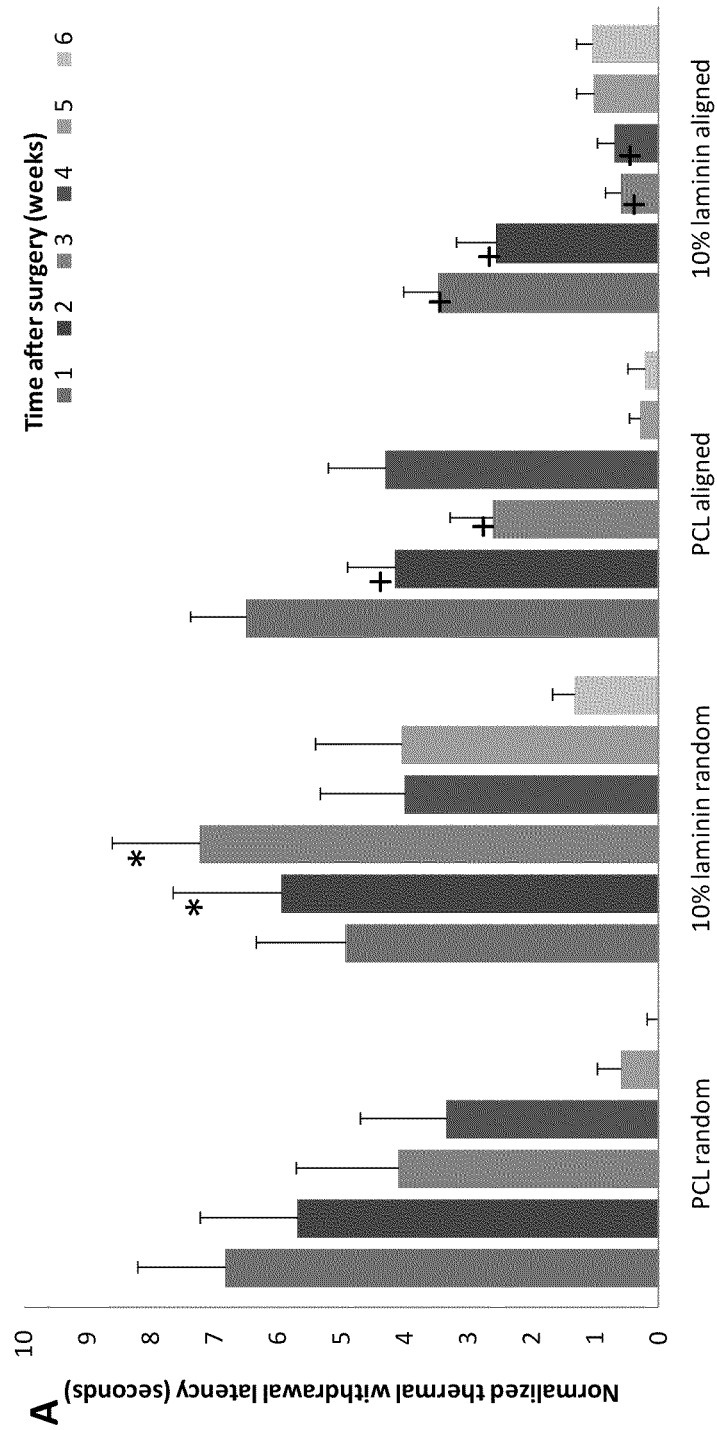
Figure 6B:
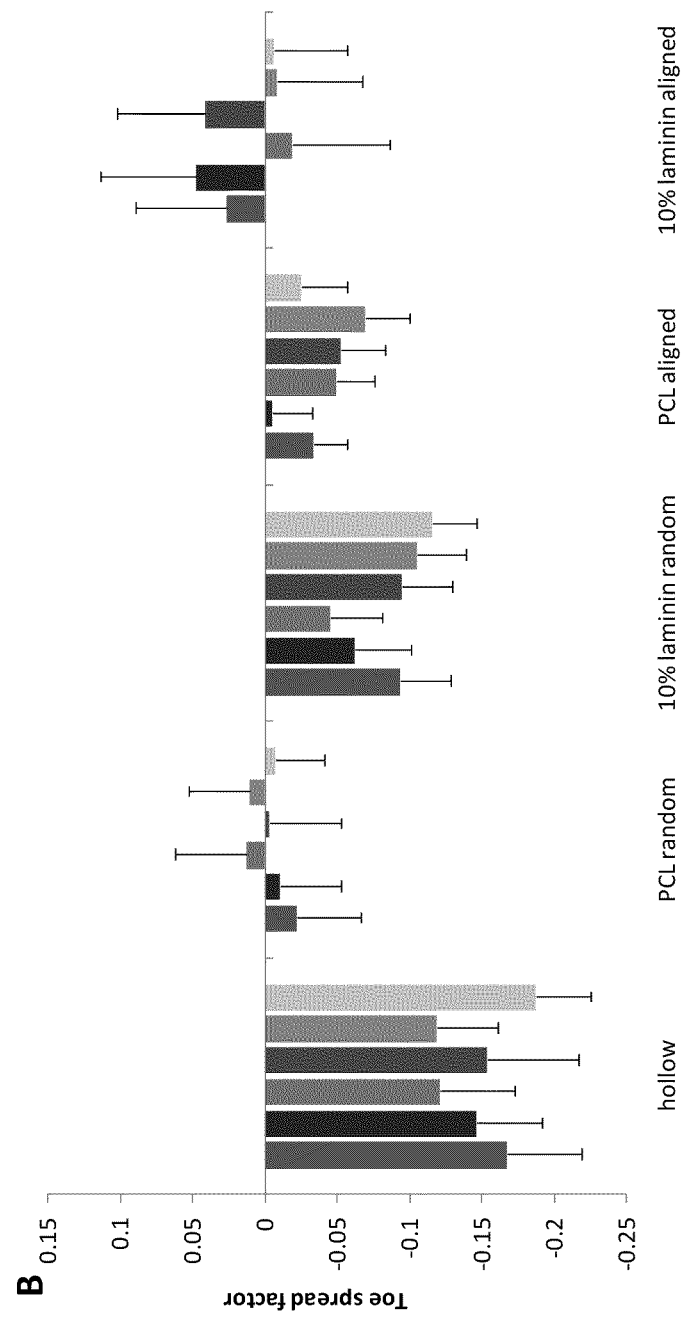

FIG. 6 of U.S. application Ser. No. 12/598,776 demonstrates the results of plating ASCs on laminin nanofibers or films prepared as described. FIG. 6 of U.S. application Ser. No. 12/598,776 represents images of comparative micrographs of ASCs cultured on laminin nanofibers (left column; FIGS. 6A, C, E, and G) and laminin films (right column; FIGS. 6B, D, F, and H).

Fiber diameter and bead area density were chosen as appropriate metrics to assess and compare morphologies among the parameter sets. As seen in the micrographs and is further supported by the data shown in FIG. 2 of U.S. application Ser. No. 12/598,776, fiber diameter increased linearly with initial solution concentration over both collecting distances. Calculated linear regressions show an almost perfectly linear correlation (R=0.99). Fiber diameter exhibits a less marked increase with increasing flow rate, though the linear correlation is equally strong (R=0.99). The same trend emerges with working distance, with increasing collector distance translating to increased fiber diameter. We generated the smallest diameter fibers, 91.5 nm (+/−8.4 nm) average, with 3% (w/v) initial concentration, 1.5 mL/hr flow rate, and 12.5 cm working distance. Overall, fiber diameter shows an approximate linear relationship to two of the physical parameters studied: concentration of initial solution and flow rate during electrospinning Although beads are a common product of the electrospinning process often regarded as defects, pioneering observations made by Martin and colleagues of the presence of the "matrisome" in basement membrane, suggested that beaded structures may be important to the activity of authentic basement membranes. Therefore, bead area density was measured to identify parameters that might control the area distribution of these matrisome-like structures. Representative images in FIG. 1 of U.S. application Ser. No. 12/598,776 show several of the parameter sets used resulted in the "matrisome" morphology. Our data demonstrate a decreasing linear relationship between bead area density and initial solution concentration (R=0.97), starting at 18.7% bead area density using the 3% (w/v) initial concentration and decreasing to only 3.4% bead area density with the 8% (w/v) initial concentration, as shown in FIG. 2 of U.S. application Ser. No. 12/598,776. However, increasing flow rate yields a linear increase in bead area density (R=0.98). Under varying flow rates between 0.5 ml/hr and 3.0 ml/hr, we measured bead area densities ranging from 9.7% to 11.5%. Finally, no obvious trend emerged with the change in distance, instead data again showed dependence on initial solution concentration. Over the two lower concentrations of 3% and 5% (wt/vol), we observed a statistically significant increase in bead area density of 15.0 to 23.8% and 8.0 to 16.0%, respectively with increased collecting distance. When compared using a student's t-test, these differences were statistically significant. With the higher initial concentration of 8% (wt/vol), the distances compared did not demonstrate statistically significant difference in bead area density, varying from 3.8% at the shorter distance to only 2.2% at the longer distance.

LNF Hydrated Morphology

Figure 1A:
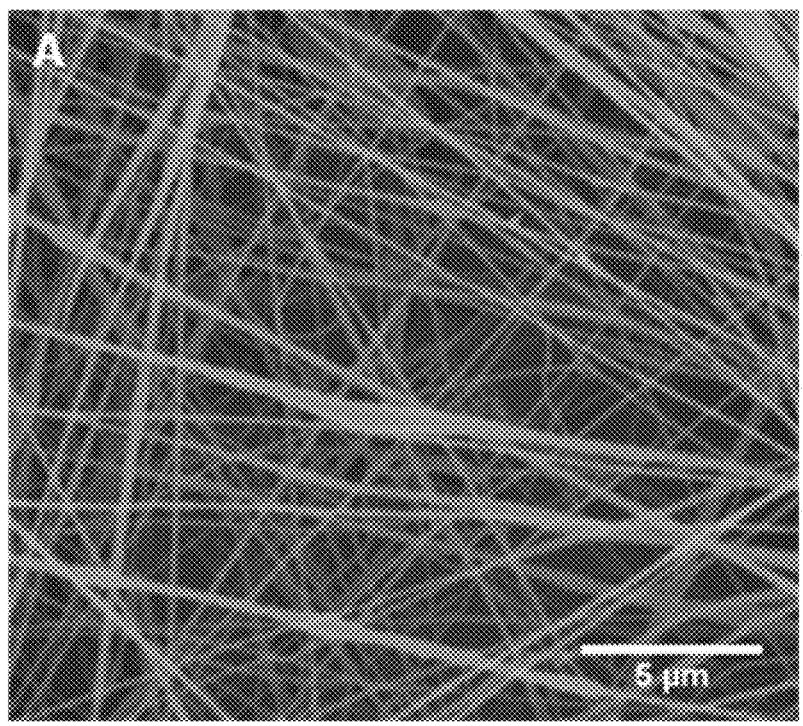
FIG. 1. Electrospun nanofibers comprising a mixture of laminin and PCL. Representative scanning electron micrographs of electrospun laminin-PCL blend nanofibers containing (A) 1% and (B) 10% laminin in total polymer weight. All other parameters were kept constant. When mean fiber diameters were compared with respect to laminin content (C), no significant differences were found ($p>0.05$). Error bars depict standard error. Fourier-transform infrared spectra indicate the presence of both PCL (arrows) and laminin (arrowheads) peaks in laminin-PCL blend nanofibers. Laminin peaks represent amine (1649 $cm^{-1}$) and amide bond (1564 $cm^{-1}$, 1649 $cm^{-1}$) regions, and PCL peaks represent C—O and C—C stretching (1293 $cm^{-1}$), asymmetric COC stretching (1240 $cm^{-1}$) and symmetric COC stretching (1170 $cm^{-1}$).
Figure 1B:
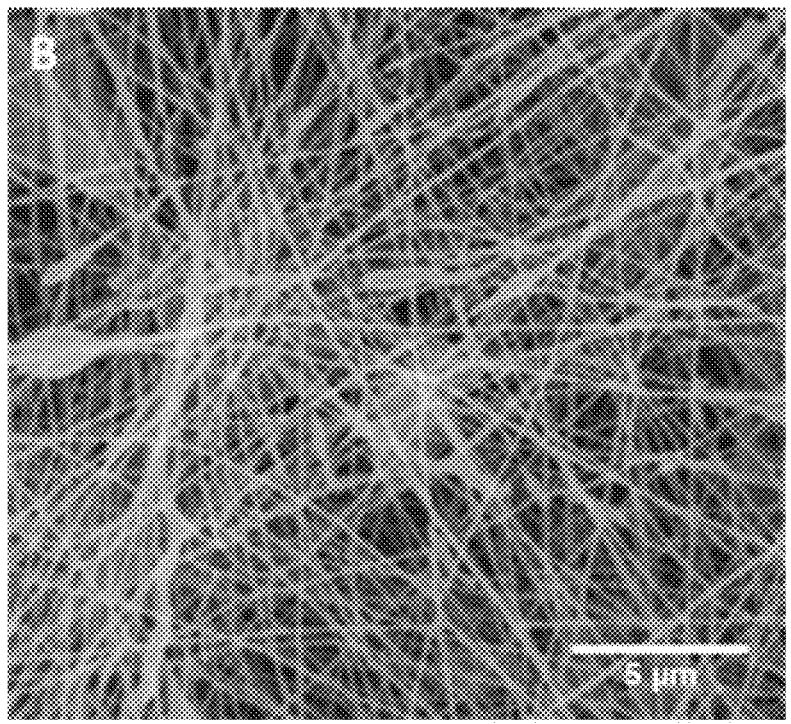
Figure 1C:
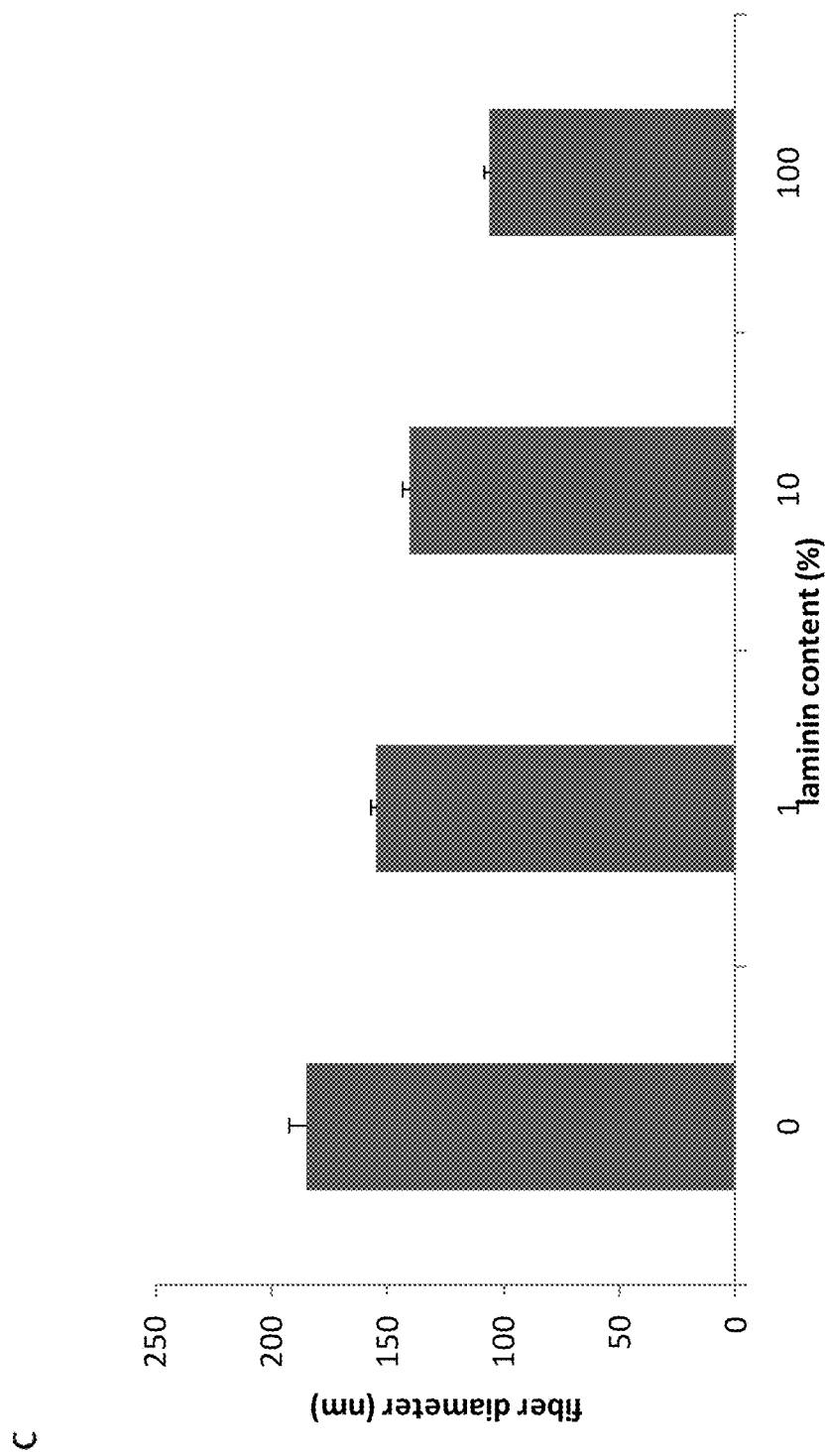
Figure 3A:
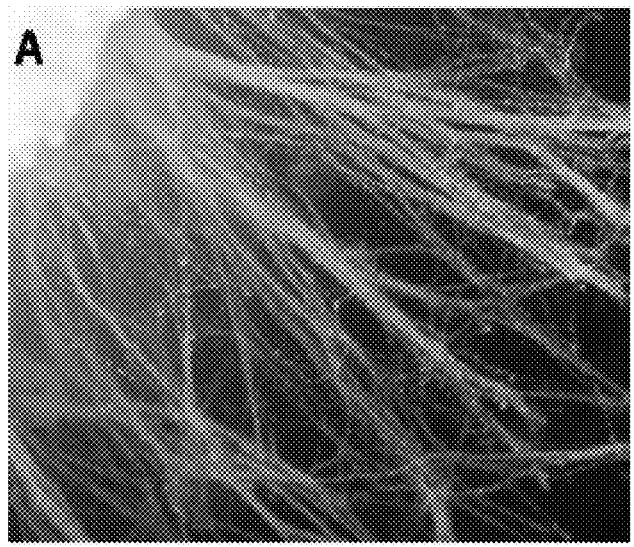
FIG. 3. Process extension of isolated DRG on laminin and laminin-PCL blend films. Representative images of murine dorsal root ganglia (DRG) extending processes on (A) 100% and (B) 10% laminin films. (C) Process extension length on 10% laminin films is not significantly different from length on 30%, 50%, or even 100% laminin films.
Figure 3B:
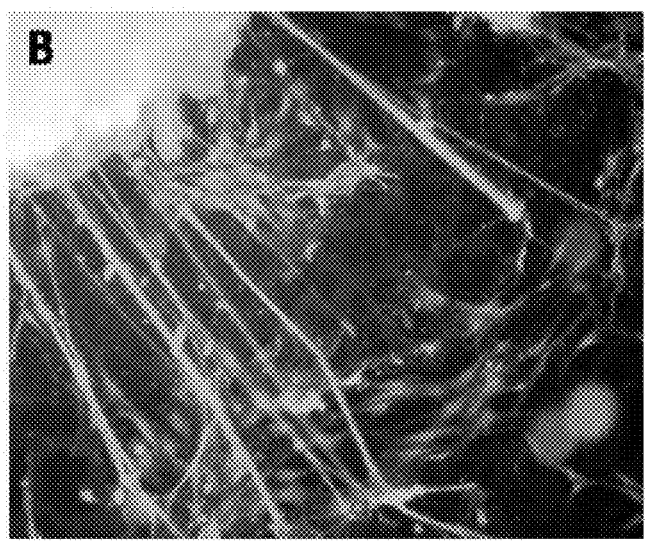
Figure 3C:
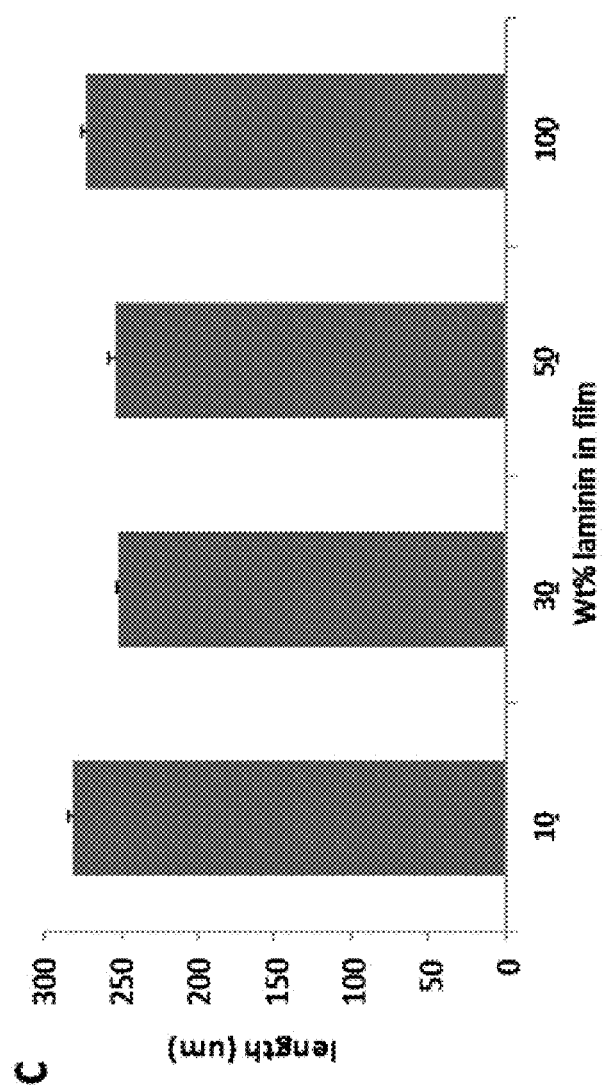

For hydration studies, the median parameters were chosen to create the meshes, with the resulting morphology shown in FIG. 1B of U.S. application Ser. No. 12/598,776. The parameter set chosen was an initial concentration of 5% laminin (w/v), flow rate of 1.5 ml/hr, collecting distance of 12.5 cm, and the constant driving voltage of 20 kV which yielded a mean fiber diameter of 141.6 nm and 8.0% bead area density. Often, biological polymers such as collagen, fibronectin, elastin, and others require chemical crosslinking to maintain their morphology in culture. Representative images of collagen changes in morphology after hydration are shown in the bottom panel of FIG. 3 of U.S. application Ser. No. 12/598,776. In the case of laminin, however, we have determined no chemical crosslinking is necessary for laminin to retain its fibrous morphology in culture. As shown in FIG. 3 of U.S. application Ser. No. 12/598,776, laminin does not swell significantly in culture medium, even after 24 hours at 37° C., while collagen almost completely loses its fibrous morphology. FIG. 4 of U.S. application Ser. No. 12/598,776 demonstrates the swelling of laminin nanofibers in aqueous media is consistently less than 10%, regardless of the amount of time the fibers are submerged. No statistically significant difference was found among the groups, including the control fibers which were not hydrated. This inherent property of laminin nanofibers to resist hydration in aqueous media makes them an attractive system to use relative to other biological polymers, as no special processing is required to crosslink and reduce or remove residual chemical crosslinking agents.

Maintenance of Bioactivity

After fibers of the desired morphology were obtained and their ability to maintain this morphology in culture medium was tested, cytocompatibility of the laminin nanofiber mesh using ASCs was investigated, a cell type which has shown promise as a tissue engineering cell source. This cell type has been shown to differentiate to a nerve-like phenotype and shows promise as a Schwann cell precursor, making ASCs applicable to peripheral nerve tissue engineering. After three days in aqueous culture conditions, we observed ASC attachment on laminin nanofibers and preferential process extension along fibers as shown in FIG. 3 of U.S. application Ser. No. 12/598,776. Additionally, we performed a cell attachment assay comparing the attachment of ASCs on laminin nanofibers to laminin films. The assay was performed under serum free conditions to exclude attachment mediated through serum proteins. Accordingly, the attachment measured was assumed to be mediated solely through the bioactivity of the substrate. Throughout the time course of the attachment study, cells showed significantly greater attachment to the nanofiber substrate than the film substrate, as shown in FIG. 4 of U.S. application Ser. No. 12/598,776. Because the cells attach more avidly to the nanofibers than equivalent saturating quantities of planar laminin, there are likely features related to size and scale of the nanofibers that are recognized by the cells.

To consider the cytocompatibility of LNFs for a nerve-like cell, PC12 cells, a cell type known to extend neurites in response to NGF, were examined. The neurite extension experiment was performed on laminin nanofibers with and without NGF stimulation to determine if the laminin substrate alone could cause neurite extension. FIG. 5 of U.S. application Ser. No. 12/598,776 depicts number of neurites per cell. Surprisingly, both groups exhibited similar neurite extension, and while the mean neurite-per-area measurement appears greater on nanofibers without stimulation, no statistically significant difference was found.

Discussion

Through the parametric study and subsequent hydration study, we were able to achieve nanoscale diameter fibers that retained their fibrous morphology in culture medium without chemical crosslinking. The positive linear correlations we found between fiber diameter and initial solution concentration and flow rate are supported by previous research in the field. With synthetic polymers such as poly(lactide-co-glycolide) and polycaprolactone (PCL), and also in other biopolymers such as collagen, and elastin, fiber diameter is generally observed to be smallest at the lowest solution concentration and flow rate, most likely due to limitations placed on the polymer content of the jet by these process parameters. Low flow rates (less than 1 mL/hr) and low solution concentrations (dependent on polymer) cause less polymer to be ejected from the syringe needle toward the collector plate at any given time, leaving a greater volume of solvent to evaporate over a longer evaporation time and extending a small volume of polymer over a greater distance in space. Generally, as we strive to mimic basement membrane in our laminin nanofibrous scaffold, we will require a range of feature heights, widths, and porosities based on the particular native membrane we hope to recreate. The relationships we have achieved through the parametric study should allow us to choose specific parameters to create the fiber diameter and morphology we desire, removing the time and expense of trial and error in the experimentation.

Additionally, the fibers generated show morphology characteristic of basement membrane. Fiber diameters from 100 nm to 280 nm were achieved herein, solidly within the ranges shown by Flemming and colleagues for human corneal epithelial basement membrane feature sizes, and within the same order of magnitude as the laminin structures shown by Yurchenco and colleagues. For example, as visible in FIG. 1 of U.S. application Ser. No. 12/598,776, electrospun laminin at lower concentrations forms structures reminiscent of matrisomes, structures composed of several basement membrane components such as type IV collagen, laminin, proteoglycans, and nidogen. It has been suggested by their group that these tetrahedral structures are a primary site for cell attachment and direction of matrix synthesis and formation. The presence of similar structures in laminin nanofiber meshes, and the observation that cells on a laminin matrix preferentially bind at these structures, supports the claim that laminin alone may provide a favorable substrate to provide cell attachment cues.

Laminin holds yet another advantage over other electrospun biological polymers such as collagens or fibrinogen: the ability to maintain fibrous morphology after exposure to an aqueous medium. Thus, laminin nanofibers are the first reported protein nanofibers suitable for in vitro studies in which the protein is native. Based on diameter measurements before and after hydration, the meshes experience a slight swelling in aqueous media resulting in a less than 10% increase in fiber diameter. Similar collagen meshes show no fibrous morphology after hydration, yielding a structure more like that of a hydrated mat or gel than a fibrous mesh. The common solution to this issue is chemical crosslinking to assist fibers in retaining their shape upon hydration; however, crosslinking itself changes the fibrous morphology significantly, destroying the porosity of the mesh and causing flattening of fibers into a ribbon-like morphology, as observed by others. Cross-linking of many proteins ablates biological activity, including laminin, which, when treated for sterilization by ultraviolet exposure, loses the ability to stimulate neurite extension of chick dorsal root ganglia. It is possible that the process of electrospinning caused a change in the molecular structure of laminin, which, while maintaining biological activity, caused the laminin nanofibers to become insoluble in aqueous media. Notably, changes in the infrared (IR) spectrum of poly(ethylene oxide) have been previously reported, suggestive of a change in the molecular structure of the fibers most likely resulting from a molecular level alignment of the individual polymer molecules.

In the present system, this structural change caused by electrospinning may be the basis for the insolubility of laminin nanofibers in aqueous media; however, this may also result from loss of water solubility as a consequence of lyophilization of the laminin preparation before dissolution in the electrospinning solvent. Laminin is essentially insoluble in aqueous, physiological buffers following lyophilization, which is a process avoided in purification of laminin for that reason.

In the attachment assay, it was shown herein that laminin in either film or fibrous form is sufficient for ASC attachment under serum free conditions. The LNF meshes, most likely due to their topography and physical similarity to basement membrane, facilitated ASC attachment over two-dimensional laminin films. Additionally, the extension of neurites by PC12 cells without standard NGF stimulation suggests laminin retains its bioactivity even in nanofiber form. PC12 cells are known to extend processes reversibly in the presence of NGF, achieving a nerve-like morphology, but cannot be forced to extend neurites without NGF by other means. In the present study, exposure to laminin nanofibers was sufficient to form processes and NGF stimulation was unnecessary. In fact, no statistical difference was found between the stimulated and unstimulated cells, suggesting the nanofibers substitute completely for the presence of NGF for neurite extension. Therefore, the present application demonstrates that the ability of the substrate to promote neurite extension was not destroyed by any of the processing methods described herein, specifically lyophilization, solubilization, and sterilization. This observation promotes LNF meshes as an ideal substrate for nervous system applications.

In conclusion, it was disclosed in U.S. application Ser. No. 12/598,776 for the first time, from which the present application is a CIP, successfully electrospun laminin-1 using HFP as a solvent under varying process parameters. The completion of the parametric study has provided guidelines by which to select parameters to create varying fiber diameters and morphologies, allowing these parameters to be tailored to the design constraints of the particular tissue. Cells attach and grow on laminin nanofibers, and nerve-like cells extend processes (neurites) without growth factor stimulation, making a nanofibrous laminin substrate ideal for many applications, particularly in nervous system tissue engineering.

Example 2

Laminin Nanofiber Mesh Substrates for Stem Cell Growth and Differentiation as Recited in U.S. application Ser. No. 12/598,776.

Methods—Embryonic Stem Cell Culture: D3 and ES-E14TG2a murine embryonic stem cells were cultured on STO or CF1 mouse embryonic fibroblast feeder layers, fed daily and sub-cultured every 2 or 3 days. The media used was DMEM+15% ES-qualified FBS supplemented with L-glutamine, non essential amino acids, pyruvate, 2-mercaptoethanol, and leukemia inhibitory factor (Chemicon). All tissue culture reagents were from GIBCO except as noted.

Fabricated meshes of laminin I nanofibers (LNFs) with fiber size (10-150 nM dia.), geometry, and porosity of authentic basement membranes were fabricated using electrospinning methods. Unlike previously described NFs synthesized from protein polymers, meshes of LNFs retain their structural features when wetted and do not require fixation by chemical cross-linking, which often destroys biological activity. Embryonic stem cells (ESCs) and multipotent stem cells from adipose tissue (ASCs) and dura mater (DSCs) attached more rapidly and avidly to LNFs than to 2-D laminin films. The rate of proliferation observed for DSCs on LNFs was greater than on 2-D films. Multipotent stem cells differentiated into cells with morphology and gene expression characteristic of Schwann (S100/nestin) and neuron-like (beta 3-tubulin) cells in serum-free, chemically defined conditions on LNFs. More neuron-like cells formed from ASCs on LNFs than on 2-D laminin films. Because the LNF meshes adhere tightly to glass and polystyrene, procedures such as immuno-histochemistry and in situ hybridization were done without detachment of substrate or cells. LNFs were stored in desiccated conditions for long periods without loss of activity. Together these observations demonstrate that LNF meshes display biological properties of basement membranes in vitro and are thus biomimetic. Furthermore, it is likely that the LNFs will be useful for many applications in vitro, including isolation and propagation of multipotent stem cells and ESCs derived from the inner cell mass, as well as in vivo, supporting tissue engineering of peripheral nerve and growth of glands and organs as scaffolds fabricated from LNFs.

Example 3

The following includes the new material upon which the present application is based, relative to the application for which it claims priority as a CIP application, i.e., U.S. patent application Ser. No. 12/598,776, filed Nov. 4, 2009.

Materials and Methods

All cell culture reagents were purchased from Invitrogen (Gibco) unless otherwise noted. Solvents for electrospinning were purchased from Sigma-Aldrich (St. Louis, Mo.), as was polycaprolactone, Mn 70-90 kDa by GPC. Laminin was isolated and purified from the Englebreth-Holm-Swarm (EHS) murine tumor in our laboratory as previously described [7].

Cell Culture

PC12 cells were obtained from ATCC and maintained in at 5% CO2 in normal growth medium consisting of DMEM/F12 (1:1) supplemented with 10% horse serum, 5% fetal bovine serum (FBS), and 1% penicillin-streptomycin. Medium was renewed every 2-3 days as needed, and cells were passaged when cell density approached $2 \times 10^5$ cells/cm$^2$. To assess cell attachment on nanofiber meshes, PC12 cells were plated at an initial seeding density of 10,000 cells/cm$^2$ in serum free media conditions. Serum was removed from the media for this assay to ensure attachment occurred due to the nanofiber geometry or composition, without the serum components that aid in cell-matrix interactions [13]. Substrates were rinsed gently at specific timepoints to remove non-adherent cells. At all time points, cells were provided adequate time for attachment but less time than the reported doubling rate of 48 hours [14]. Cells were then fixed for 30 minutes at room temperature using 4% paraformaldehyde (PFA), stained with DAPI for visualization, and imaged. For the neurite extension assay with PC12 cells, cells were plated at an initial seeding density of $2.5 \times 10^4$ cells/cm$^2$ in serum free medium onto glass coverslips coated with nanofibers of various compositions. For groups receiving nerve growth factor (NGF) stimulation, NGF was added after two hours to a concentration of 50 ng/mL. Cells were imaged every day for five days in culture. On the fifth day, cells were fixed in 4% PFA for 30 minutes at room temperature, stained with DAPI for visualization, and imaged. Processes were measured and counted, and statistical comparisons of both length and number were made using a one-way ANOVA with Tukey's post hoc testing (Minitab, State College, Pa.), with significance asserted at $p<0.05$.

Dorsal root ganglia (DRG) were isolated for culture from neonatal FVB/N mice which contain a yellow fluorescent protein (YFP) reporter for β-III-tubulin expression in the developing peripheral and central nervous systems [15]. The DRG were gently plucked from the exposed spinal column, capsules surrounding the DRG were mechanically removed using fine forceps, and the whole DRG body, consisting primarily of peripheral neuron cell bodies, was allowed to attach to the culture surface (tissue culture plastic for control studies, or nanofibers on glass coverslips) in a minimal amount of medium for two hours before culture medium was added. Growth medium was Ultraculture, with or without 10% FBS, and nerve growth factor (NGF) was added as a growth stimulant up to 100 ng/mL. For neurite extension studies, DRG were allowed to grow in NGF-supplemented medium conditions for up to five days. Growth was imaged daily, and on the fourth day, cells were fixed as described above and imaged using both light microscopy and fluorescence to detect the YFP signal. At least three DRG per condition were analyzed, with at least ten processes per DRG measured. Length was measured from the edge of the original DRG body in a straight line to the end of the process farthest from the initial DRG border. Statistical comparisons of length were made using a one-way ANOVA with Tukey's post hoc testing (Minitab, State College, Pa.), with significance asserted at $p<0.05$.

Preparation of Mixtures (Blends of Protein and Polymer)

For the experiments described below, either 5% or 8% w/v of total polymer (protein+synthetic polymer) in HFP were used for electrospinning fibers. At either amount, the ranges of laminin percentages of total polymer tested include 0.1%, 0.5%, 1.0%, 10% and 50% (w/w) relative to the synthetic polymer. Laminin percentages of the total amount of polymer used are indicated on the Figures and in the Results described below. In the experiments described below, PCL is the synthetic polymer.

Blend Fabrication

To fabricate blend films or nanofibers, appropriate amounts of dry PCL and laminin were dissolved independently in 1,1,1,3,3,3-hexafluoro-2-propanol (HFP 99.5%, Acros Organics) and then combined to create the desired ratio in solution. For film fabrication, the solution was dispensed onto 12 mm diameter glass coverslips, and the solvent was allowed to evaporate, leaving a thin film of polymer. For electrospun nanofibers, the solution was loaded into a syringe equipped with 18-20 G blunt tipped needle, and mounted into an Aladdin programmable syringe pump (World Precision Instruments, Sarasota, Fla.). To collect samples for materials analysis such as mechanical testing or scanning electron microscopy (SEM), a collector plate covered with aluminum foil was 10-20 cm below the tip of the needle and electrically grounded. When samples for cell culture were created, 12 mm diameter glass coverslips were placed on top of the grounded collector plate. A high voltage power supply (Gamma, Ormond Beach, Fla.) provided positive voltage (10-20 kV), and the syringe pump maintained a steady flow rate (0.5-5.0 mL/hr).

To create patterns for aligned electrospun nanofibers, a conducting material (aluminum or gold) was used to create a gap across an insulating material (glass or air). Aluminum samples were fabricated in the laboratory using aluminum foil and glass coverslips, while gold samples were fabricated by Nathan Swami's group, following previously published protocols [10]. These patterns were utilized in place of the grounded collector described above, and electrospinning proceeded using the same parameters. After electrospinning, all samples, regardless of application, were allowed to dry for at least 24 hours and then lyophilized for an additional 24 hours to remove any residual solvent.

Blend Characterization

Samples for SEM were cut from the aluminum foil, mounted on aluminum stubs (Electron Microscopy Sciences, Hatfield, Pa.), sputter coated with gold using a BAL-TEC SCD005 sputter coater, and imaged using a JEOL JSM6400 Scanning Electron Microscope (SEM) with Orion image processing at 15 kV accelerating voltage. Diameter measurements were made using the measure tool in Image J (open source software available through NIH), with at least 50 measurements per sample. Care was taken that each measurement represented an independent fiber in the image.

Fourier transform infrared (FTIR) spectroscopy was used to characterize the blend mesh components, to ensure both PCL and laminin spectra were visible. An Alpha FT-IR spectrometer (Bruker Optics, Inc., Billerica, Mass.) was used in attenuated total reflectance mode. Dry polymer samples, stock polymer as received or isolated, or polymeric nanofiber meshes, were placed on the field and analyzed. Spectra were generated using Opus software and compared for characteristic peaks of both PCL and laminin.

For mechanical testing, rectangular samples at least 10 mm in length and 5 mm in width were separated from the aluminum foil and mounted into mechanical grips on an Instron 5543 (Instron, Norwood, Mass.) using BlueHill 2 software. An initial strain of 0.2% was set, and the sample was loaded uniaxially at a rate of 10% strain per minute. Stress versus strain curves were measured and characterized by Young's modulus, yield strength, and ultimate tensile strength (UTS).

For gel permeation chromatography (GPC) to determine molecular weight changes and degradation properties over time in aqueous media, nanofiber meshes were incubated in PBS at 37° C. with gentle agitation for up to six weeks. At each time point, PBS was aspirated and samples were lyophilized overnight to remove residual solvent. Samples were then dissolved in HPLC-grade tetrahydrofuran (THF), filtered through 0.2 µm filter, and loaded into vials with a septum for GPC. Molecular weight was measured by GPC (THF, 20° C., 1.0 ml/min) against polystyrene standards on a Hewlett-Packard instrument (series 1100 HPLC) equipped with Polymer Laboratories 5 µm mixed-C columns and connected to refractive index (Viscotek LR 40) detector. Data were processed with the OmniSEC software (version 4.2, Viscotek Corp).

Alignment was characterized utilizing both manual angular orientation measurement as well as calculating the vector produced by Fast Fourier Transform (FFT) of the image. For angular measurements, the axis of alignment was chosen as perpendicular to the conducting electrode edge, and fiber angles were measured from that axis. A minimum of 20 angular measurements were made per image. Applying FFT methods to digital images yielded a frequency domain representation. In addition, a magnitude plot of the frequency domain provided information about the orientation of edges present in the image. Scanning electron micrographs were submitted to FFT. When the edges of the fibers were parallel to each other, as in the aligned samples, the FFT displayed a narrow distribution of intensities around a center which indicated the direction perpendicular to the edge orientation. When edges of the fibers were random, the intensity distribution widened into a circular distribution. To quantify the intensity distribution, the mean intensity was computed at various angles about the center of the image in a circular ring with inner radius equal to one eighth and the outer radius equal to one quarter of the image size. From this mean intensity plot, full width at half maximum about the peak intensity value were calculated. When normalized with respect to 180°, this distribution yielded a value between zero and one, defining the degree of alignment of the edges in that image. In this distribution, zero represented completely random, or lack of, orientation, and one represented completely aligned nanofibers.

Rat Tibial Nerve Transection and Conduit Repair

To create polycaprolactone (PCL) microfiber conduits for the in vivo study of laminin-PCL blend nanofiber meshes, a 1.6 mm diameter stainless steel rod (McMaster-Carr, Los Angeles, Calif.) was cut to 30 cm length and mounted into a custom, self-centering chuck connected to a motor (ZDM3581T, Baldor Vector Three Phase Motor and H2 Vector Drive, Ft. Smith, Ak.) using non-conductive couplers. The chucks slide on a custom rail with a freely rotating tail chuck, and the entire system is housed in a ½ inch thickness HDPE enclosure. An initial solution of 20% (w/v) PCL in HFP was loaded into a syringe, mounted in the syringe pump (Aladdin 1000, World Precision Instruments, Sarasota Fla.), and situated 12-14 cm away from the center of the rotating mandrel.

The positive voltage lead of the high voltage source (Gamma, Ormond Beach, Fla.) was connected to the 18G needle, and the mandrel was grounded using the ground lead. Mandrel rotation speed was set to 100 rpm to prevent mechanical alignment that occurs with higher rotation speeds. The solution was dispensed at 2 mL/hr, and simple translating motion was used to ensure complete coverage of the 30 cm mandrel. After electro spinning, the conduit material was dried under vacuum, then cut into 15 mm segments and removed from the stainless steel rod and sterilized for implantation. The resulting conduit had an inner diameter of 1.6 mm and a length of 15 mm. Nanofiber sheets of randomly oriented PCL nanofibers, randomly oriented 10% laminin nanofibers, or longitudinally aligned PCL nanofibers were folded in half and placed into the lumen of the conduit. Conduits were sterilized under ultraviolet (UV) light overnight, followed by two 30 minute washes in 70% ethanol and three 30 minute washes in sterile water. Conduits were maintained in sterile phosphate buffer solution (PBS) until implantation.

Female Sprague Dawley rats weighing 250 g at the time of surgery were anesthetized using isoflurane to effect and maintained under anesthetic for the duration of the procedure. The surgical site was shaved and prepped using aseptic technique, and ketoprofen (4 mg/kg) was administered subcutaneously as an analgesic to relieve post-operative pain. A skin incision was made along the length of the tibial axis on the medial side of the lower extremity, providing access to the tibial nerve. The nerve was gently freed from the surrounding musculature and transected. A 5 mm segment was removed and the nerve was allowed to retract, leaving a 10 mm gap between the proximal and distal ends. The 15 mm conduits were placed in the gap, and nerve stumps were pulled 2.5 mm into each end and sutured through the epineurium with 10-0 nylon suture (Ethilon). The incision was closed using subcuticular 4-0 vicryl sutures (Ethilon) and sealed with VetClose (Butler Animal Health Supply, Dublin, Ohio). Bitter orange ointment (ARC Laboratories, Atlanta, Ga.) was applied to the foot to prevent self-mutilation. Ketoprofen (4 mg/kg) was administered subcutaneously once daily as an analgesic for three days post-surgery, and rats were housed separately with access to food and water ad libitum in a 12 hour light/dark cycle for the duration of the study. Weekly motor and sensory follow up testing was conducted on all experimental groups.

Motor and Sensory Testing

To examine sensory recovery, measurement of thermal withdrawal latency was conducted using a paw thermal stimulator which measures the latency interval between stimulus application and paw lifting. This method has been previously described for analysis of sensory function in lower limb nerve injury [16]. Briefly, the plantar test system (IITC Life Science, Woodland Hills, Calif.) consists of a plastic chamber that sits on a clear elevated floor and is temperature regulated at 30° C. Animals were allowed to acclimate in the chamber for 15 minutes. A radiant heat source mounted on a movable holder beneath the glass floor was used to deliver a thermal stimulus to the plantar side of the hind paw. To prevent thermal injury, the light beam was programmed to stop automatically after 20 seconds if the animal failed to withdraw its paw. Baseline levels were determined prior to surgery, and the thermal intensity was adjusted to provide a 4-6 second latency period in normal, non-injured rats. At least three latencies were measured for each hind paw per test session. The three scores were averaged and compared using a general linear model ANOVA with crossed factors and Tukey's posthoc testing with significance asserted at $p<0.05$.

To assess motor recovery, walking track analysis was performed to assess the animals' mobility and gait. The hind feet were dipped in dilute India ink, and the rats were allowed to walk down a 10×60 cm corridor into a darkened box. The floor of the corridor was covered with removable paper used to record the animals' paw prints. At least three clear paw prints were selected from each walking track and the parameters of print-length, toe-spread (distance between first and fifth toes), and intermediary toe-spread (distance between second and fourth toes) were measured, as these particular measurements have been shown to be most indicative of specific gait changes due to tibial nerve injury. The contralateral paw print was measured to determine the normal values and calculate the print length, toe spread, and intermediary toe spread factors. In all cases, the maximal distance was measured. The formula of Bain and coworkers was used to calculate the tibial function index (TFI) with a value of 0 representing normal function and a value of −100 indicating complete loss of function [17]. Both the TFI and the toe spread factor for animals from each group were compared using General Linear Model ANOVA with crossed factors in Minitab 15 statistical software. Pairwise comparisons were made with Tukey posthoc test, with significance asserted at $p<0.05$.

End-Point Testing: Electrophysiology and Histological Analysis

At the end of the study, animals were tested for nerve conduction and electromyography (EMG) before tissue was harvested for histology, following established protocols [8] For electrophysiology, the animal was anesthetized and the initial surgery site exposed. The conduit or healthy tibial nerve and a small segment proximal and distal to the injury were freed from surrounding tissue. Neurosign disposable bipolar probes (Magstim, Wales, UK) were placed on the exposed sections, 15 mm apart. Both proximal and distal electrodes were stimulated in turn, utilizing a square pulse of 0.02 ms duration and 10-20 V amplitude on a Teca Synergy N-EP system (Oxford Instruments, Oxfordshire, UK). For assessment of muscle reinnervation, the distal electrode was moved to the surface of the gastrocnemius muscle to record EMG activity.

After electrophysiology, animals were euthanized and tissue was harvested and fixed overnight in 4% paraformaldehyde. Post-fixation, samples were moved to 30% sucrose in PBS solution for up to three days at 4° C., after which samples were embedded in O.C.T. Compound (Tissue Tek) and frozen for cryostat sectioning. Using a Leica CM1950 Cryostat (Leica, Wetzlar, Germany) 8-14 micron thick sections were cut from either transverse or longitudinal sections of the nerve, and immunohistochemistry was performed to indicate the presence of regenerating axons (NF160, 1:500, Abcam). For immunohistochemistry, sections were washed in 0.1% saponin in PBS and incubated in a blocking solution consisting of 4% normal goat serum (NGS), 1% bovine serum albumin (BSA), and 0.1% saponin for one hour at room temperature. Primary antibody was reconstituted in the blocking solution and applied to sections. Sections were then incubated overnight at 4° C. Before application of the secondary antibody, samples were washed in 0.1% saponin in PBS. Sections were then incubated in dilutions of secondary antibody (Alexa Fluor546 goat anti-rabbit IgG) for one hour at room temperature. Sections were washed, dried, and mounted using VectaShield hard mount with DAPI (Vector Laboratories, Servion, Switzerland). Sections were imaged using a Nikon Eclipse C1 confocal microscope Results (Example 3)

Blend Fabrication and Characterization

To characterize the blended laminin-PCL nanofibers, we examined mesh morphology using scanning electron microscopy, polymer content using Fourier Transform Infrared Spectroscopy (FTIR), changes in mechanical properties using uniaxial tensile testing, and degradation properties using gel permeation chromatography. We successfully fabricated blend nanofiber meshes containing 1% and 10% laminin content by weight, as shown in FIG. 1A-B. The fiber diameters of these meshes were measured from 100 to 200 nm in mean diameter, within published ranges of native basement membrane feature size (FIG. 1C) [11].

Figure 1D:
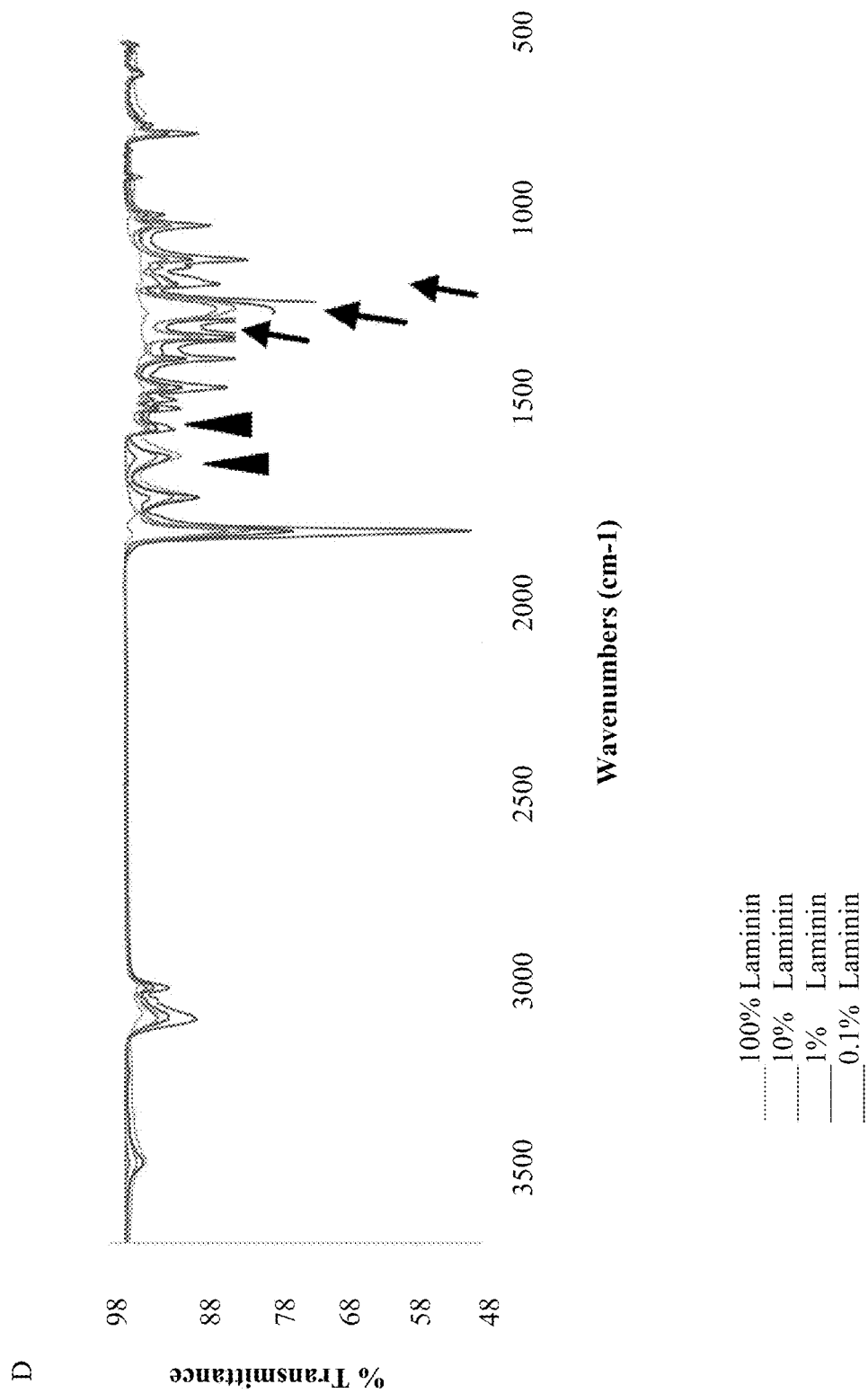

To ensure both PCL and laminin were present in the blend meshes, we considered the FTIR spectra (FIG. 1D). The FTIR spectra describe the bond angles present in the sample, and when used in attenuated total reflectance (ATR) mode, nanofibers can be used as the sample for analysis. Characteristic peaks of each polymer are indicated on the spectra and confirmed the presence of both polymers. Interestingly, increasing laminin content yielded greater laminin peaks and higher PCL content yielded greater PCL peaks in near proportion to respective compositions. Since samples of similar total polymer content were used for analysis, it is possible signal strength in this case does correlate with amount of polymer present.

Also see FIG. 9.

Figure 2A:
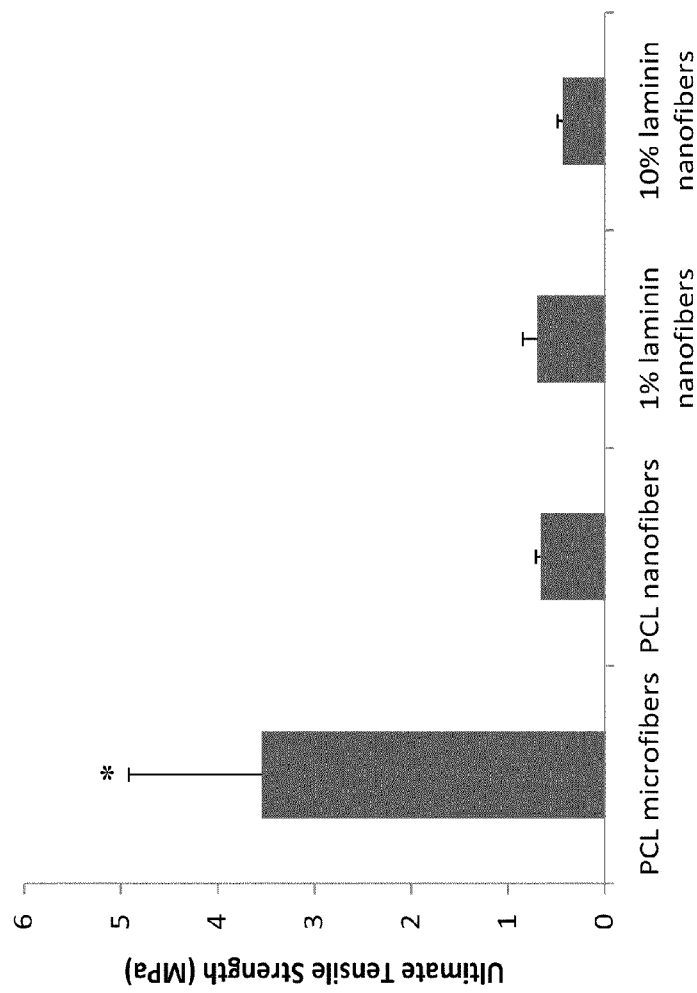
FIG. 2. Tensile and degradation properties electrospun nanofibers comprising a mixture of laminin and PCL. (A) Young's moduli, (B) yield stress, and (C) UTS were calculated from stress straining curves generated by uniaxial tensile testing. Young's moduli were estimated in the linear portion of the curve, between 5 and 25% strain, with UTS was reported as the maximal stress on the curve. * indicates statistically significant difference ($p<0.05$) between microfiber group and all other groups. (D) $M_w$ as measured by GPC did not change significantly over the lifetime of the conduit, regardless of the laminin content used. While a slightly decreasing trend is visible in the data, the change was not significant over time ($p=0.325$). Data were analyzed using a general linear model ANOVA with crossed factors in Minitab statistical software. Significance was asserted at $p<0.05$. All error bars depict standard error.
Figure 2B:
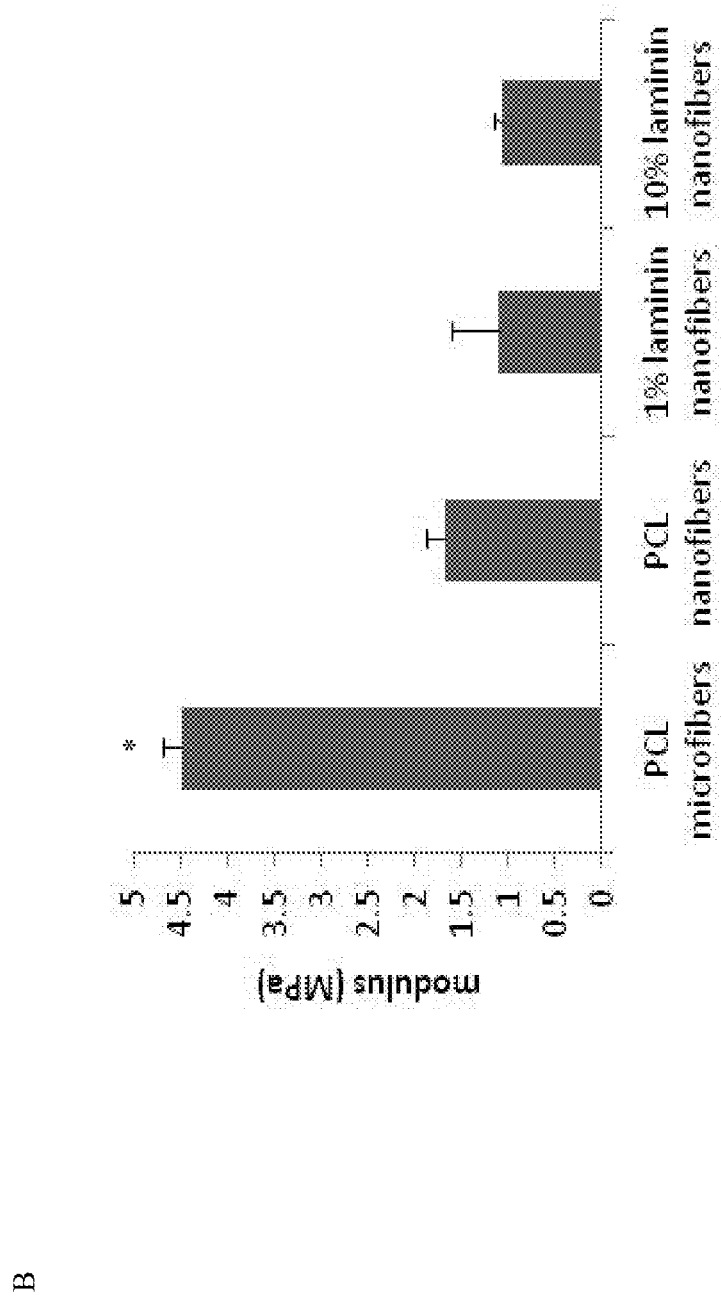
Figure 2C:
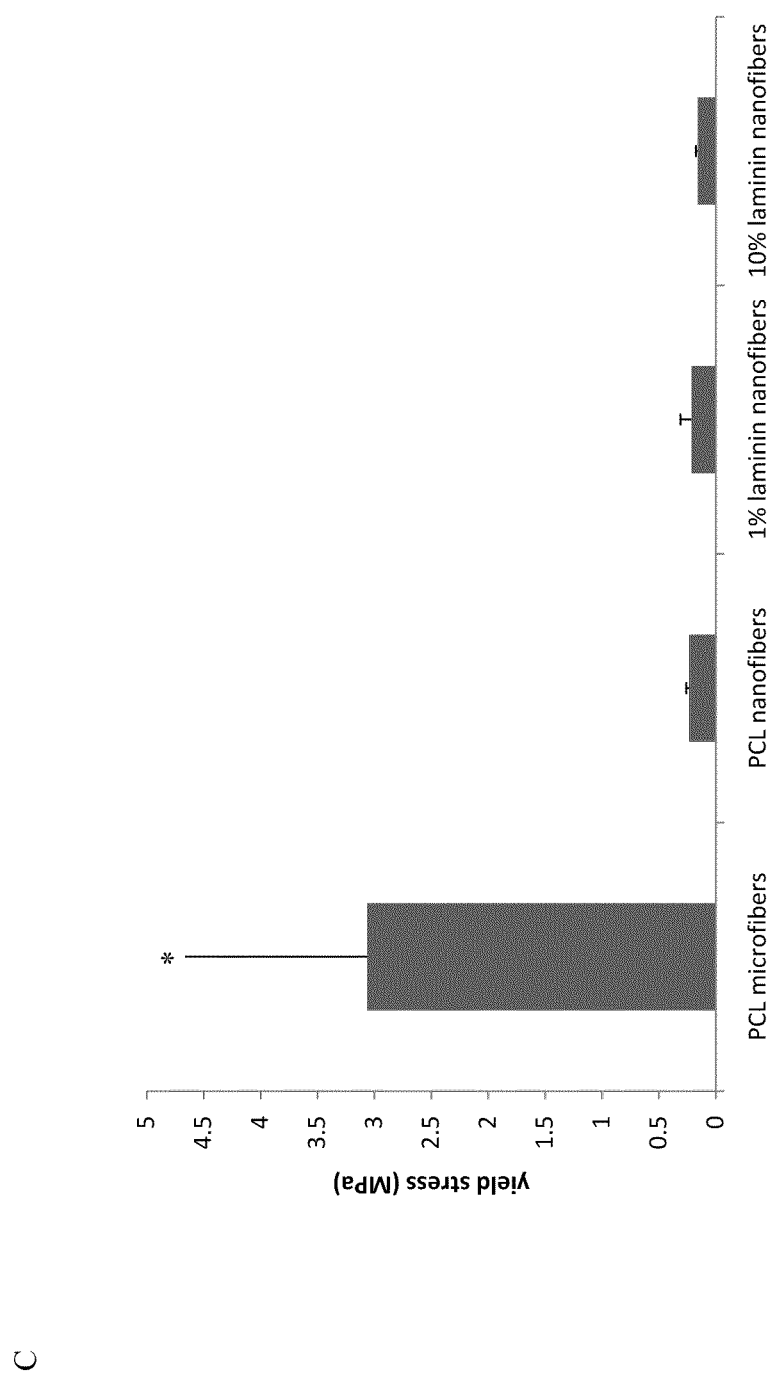
Figure 2D:
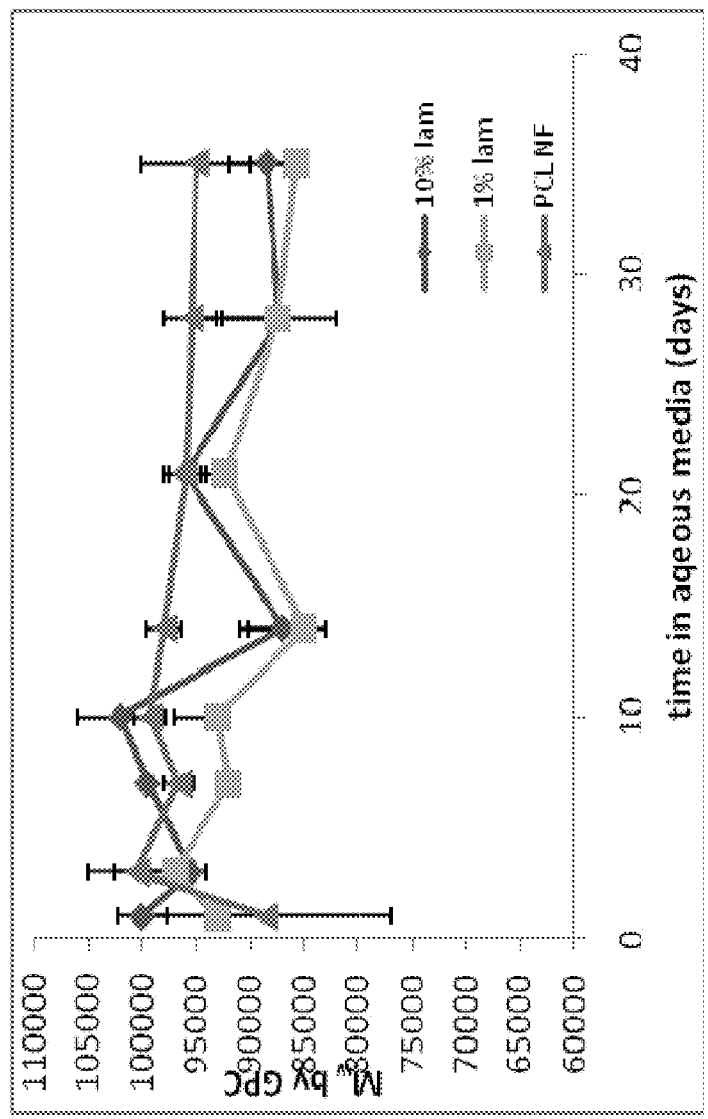

Uniaxial tensile testing satisfied our concern that laminin content may affect critical mechanical properties of the mesh. Since significant tension should not be experienced in the healing environment of the peripheral nerve, and in fact surgeons strive to create a tensionless environment using nerve guidance conduits, minor differences in tensile strength should not lead to conduit failure. When comparing Young's modulus, ultimate tensile strength (UTS), and yield strength, a range of comparisons which span the stress strain curve of these materials, we saw no significant difference among the blends of various laminin content (FIG. 2A-C). In addition, to show that laminin content at or below 10% of the total polymer weight did not play a significant role in the degradation properties of the material, we compared weight-averaged molecular weight (Mw) by GPC over six weeks, the length of our preliminary in vivo study. From this analysis, shown in FIG. 2D, we observed no significant difference in Mw over time. For the considerations of nerve repair, we found no detriment in terms of mechanical or degradation properties to prohibit the use of laminin as up to 10% polymer weight as a substrate for regeneration.

Assessment of Bioactivity

Having chosen laminin specifically for its inherent properties which promote cell attachment and neurite extension, we sought to verify that this material does indeed retain these properties after processing into a blended nanofiber with the synthetic polymer PCL. Initial studies showed 10% laminin content in film substrates for cell culture yielded process extension from murine dorsal root ganglia (DRG) of length and number not statistically different from that on 100% laminin (FIG. 3). While further studies may elucidate the threshold content for laminin activity, for the remainder of our studies, we established 10% laminin content as the maximum laminin required to maintain bioactivity.

Figure 4A:
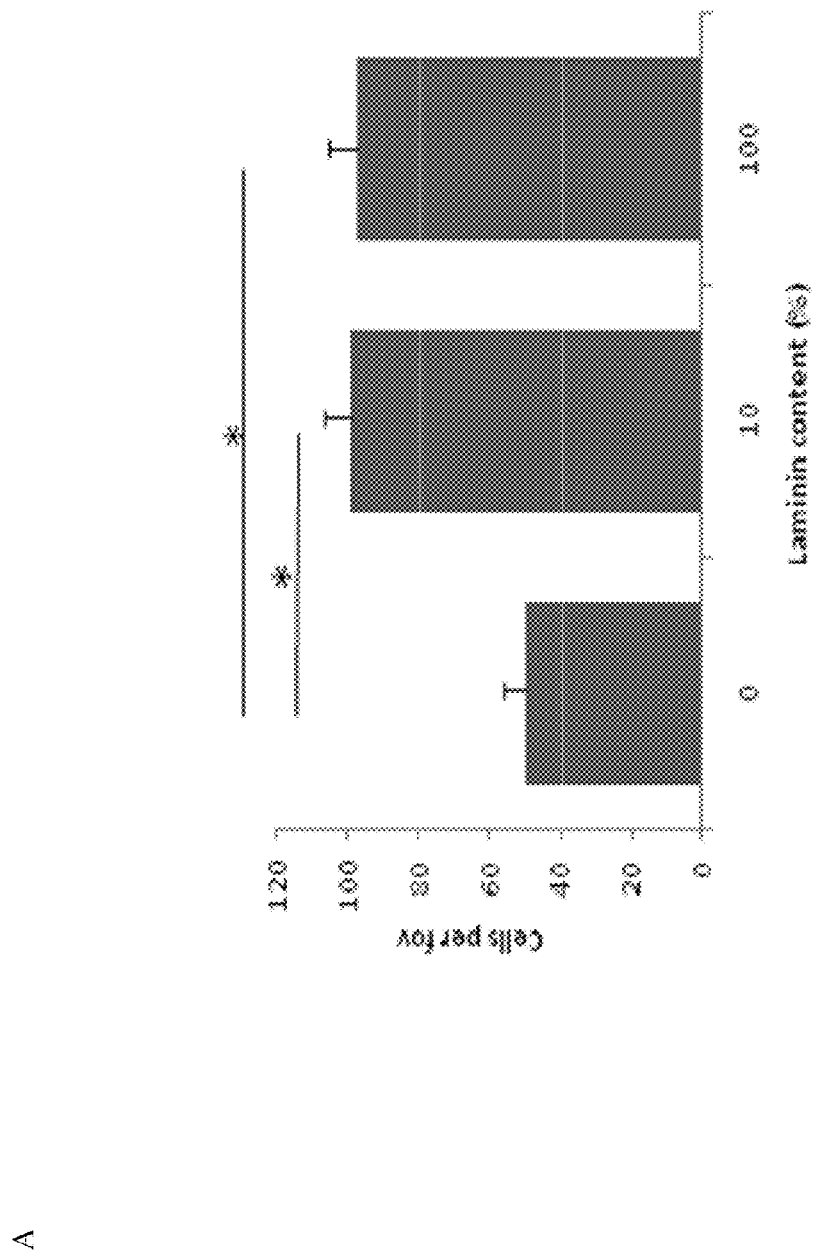
FIG. 4. Attachment and process extension on laminin and laminin-blend nanofibers. (A) PC12 cell attachment in serum free media on laminin-PCL blend nanofibers. * indicates $p<0.01$. (B) Neurite extension length from DRG is not statistically different on laminin or laminin-PCL blend nanofibers, as illustrated by representative images of murine DRG neurite outgrowth on (C) 100% and (D) 10% laminin nanofibers after 4 days in NGF-supplemented culture conditions. All error bars represent standard error.
Figure 4B:
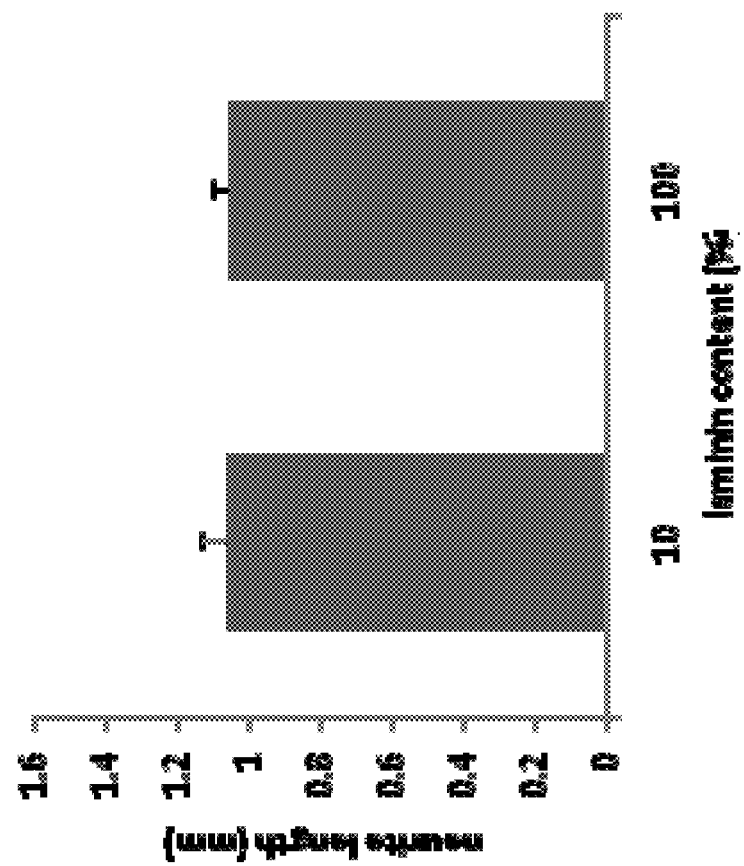
Figure 4C:
Figure 4D:
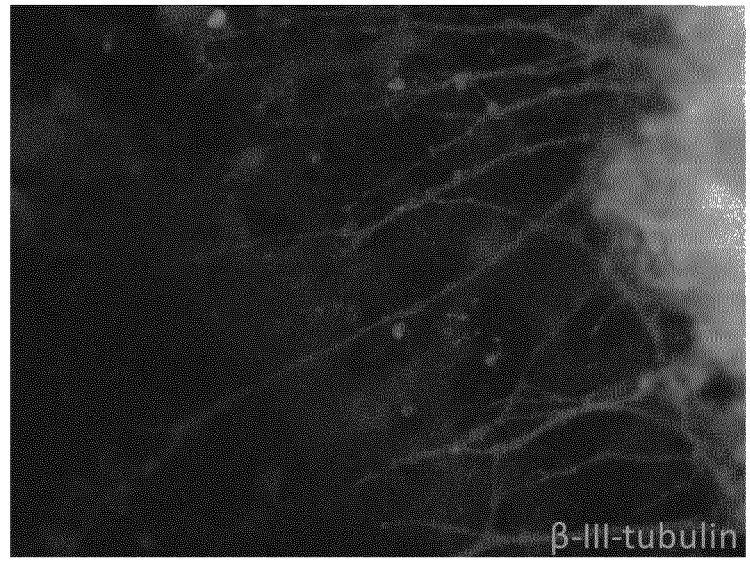

PC12 cells were chosen for their neuron-like process extension, but provide an additional benefit here: they will not remain attached to tissue culture polystyrene without serum unless an adhesive surface is provided. To ascertain that laminin maintains its cell adhesive properties when blended with PCL, PC12 cell attachment was investigated (FIG. 4A). After 24 hours, sufficient time for attachment but less than the doubling time of the cells, attachment to blend meshes was quantified. While very few cells were able to attach to PCL nanofibers alone, no significant difference in attachment was observed between 10% and 100% laminin nanofibers. In addition, to examine the feature of PC12 cells more relevant to clinical application in peripheral nerve regeneration, we examined PC12 process extension on blend nanofibers. We found PC12 cells extend processes longer than the diameter of the cell body on blend nanofiber substrates, regardless of whether NGF is provided as a soluble signal.

To further verify that blending laminin with PCL allows for the retention of laminin bioactivity, we assessed neurite outgrowth from murine dorsal root ganglia over a four day period. Utilizing a β-III-tubulin driven YFP reporter transgenic mouse, we were able to record the functional outcome of β-III-tubulin expression in our studies as well. Shown in FIG. 4B-D, we saw significant outgrowth all around the DRG, regardless of whether laminin content of the nanofibers was 10% or 100%, and were able to detect no difference in length of processes. In addition, primary neurons dissociated from DRG were observed to extend processes on blend nanofibers with no significant difference in length or number of processes than seen in previous studies on pure laminin nanofibers [7]. We chose neurite length as the metric for comparison because length, rather than number, size, or another metric, is most indicative of the time to healing of an injured nerve fiber. Longer extensions equate to faster regeneration, and atrophy of the end organ is prevented when a functional connection is made, even if that connection is weaker (fewer axons) than the original connection. Once the functional connection is successful, the nerve can continue to grow and expand its number of axons and the number of myelinated axons.

Oriented Nanofiber Meshes and Directional Outgrowth

Figure 5A:
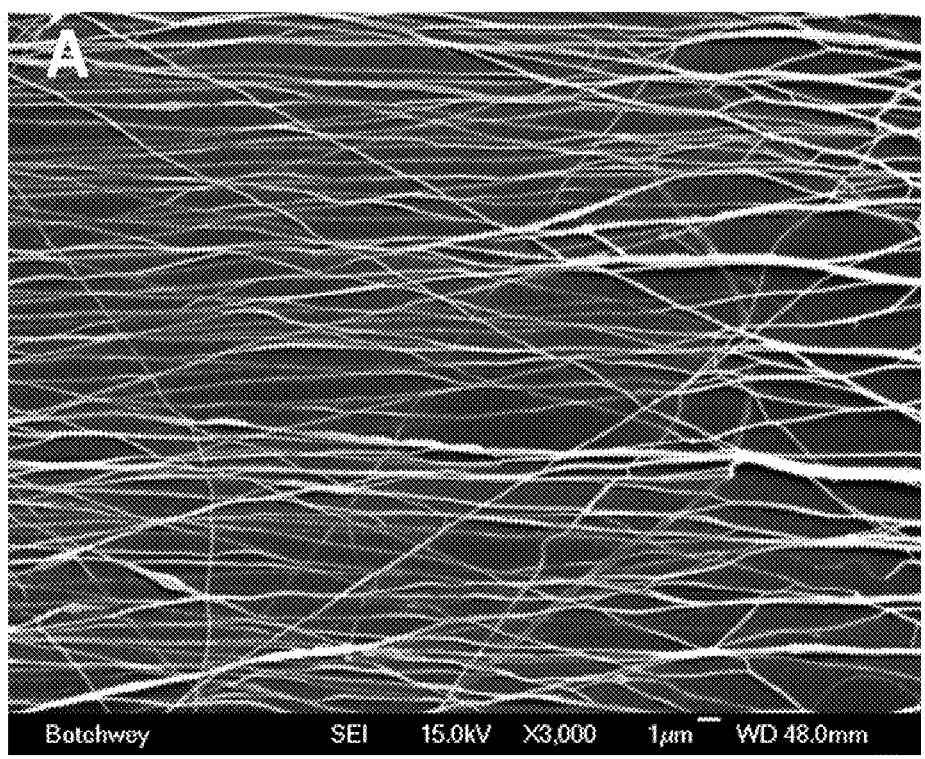
FIG. 5. Stretching and alignment of laminin-PCL blend nanofibers using insulating gap. (A) Representative scanning electron micrograph of aligned 10% laminin blend nanofibers. (B) These nanofibers show significant stretching across the gap, resulting in decreased fiber diameter in aligned samples, regardless of initial total polymer weight (5% or 8%). (C) Degree of alignment was calculated using angular deviation from the axis of alignment, and no significant differences were found among aligned samples of PCL or laminin-PCL blend. (D) FFT calculations of normalized full width of half maximum frequency showed no statistically significant difference in degree of alignment between PCL and laminin-PCL blend nanofibers. Representative images of (E)
Figure 5B:
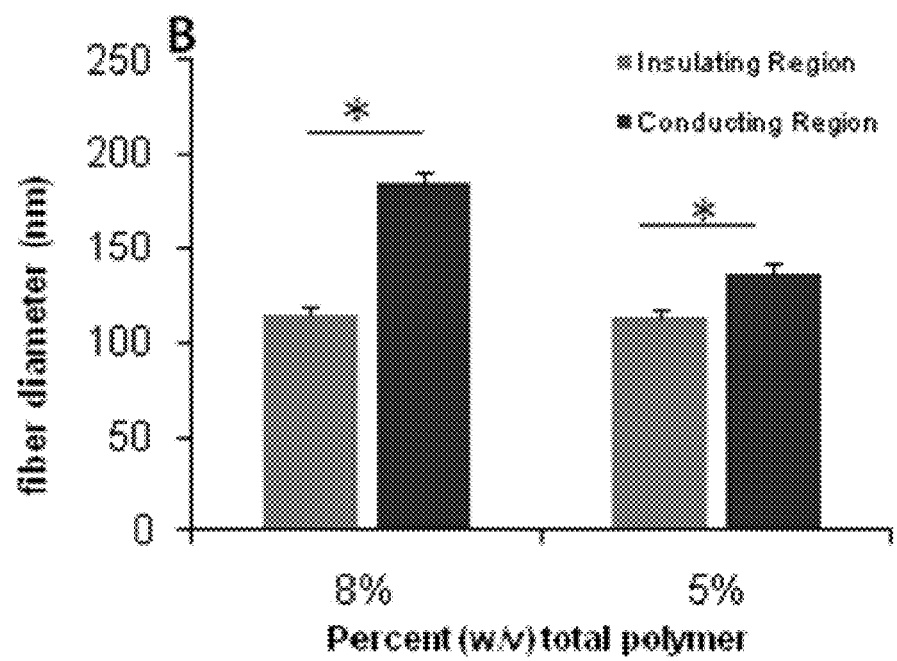
Figure 5C:
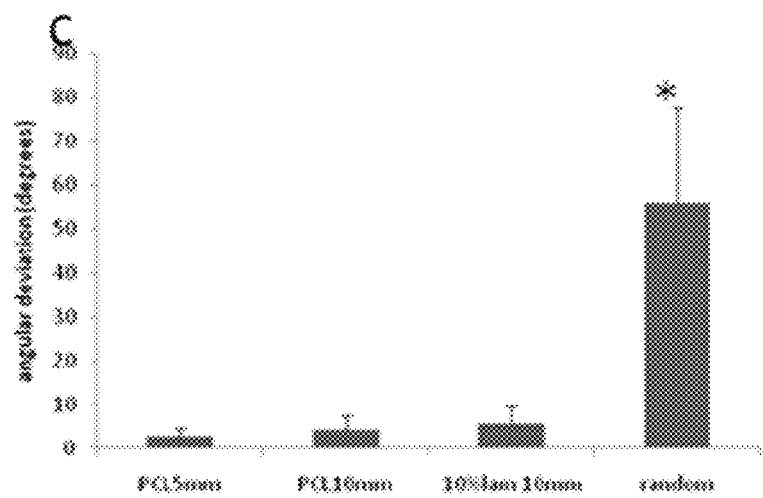
Figure 5D:
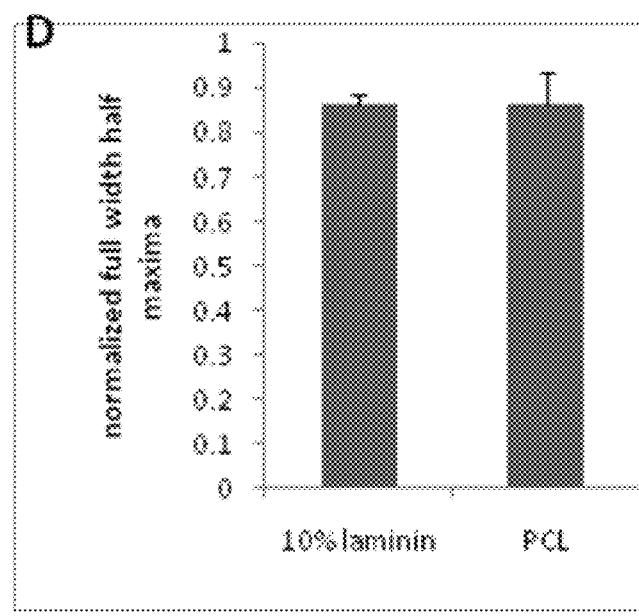
Figure 5E:
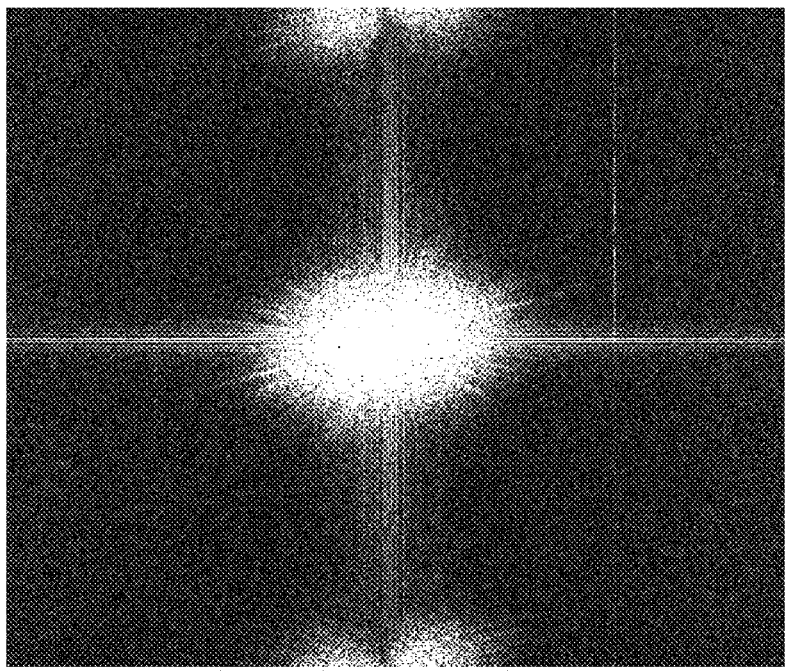
Figure 5F:
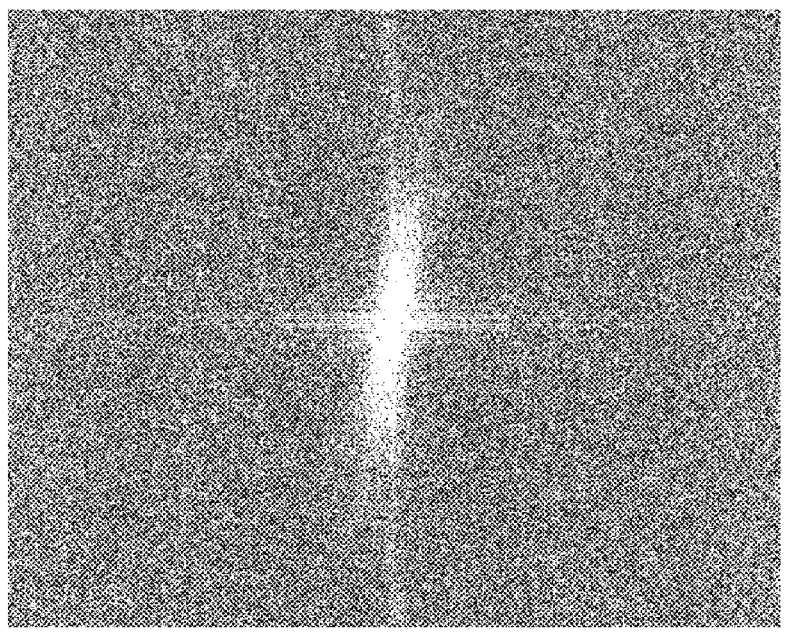

Though laminin nanofibers, or PCL-laminin blend nanofibers with at most 10% laminin content, provide sufficient cues to encourage attachment and outgrowth, we fabricated aligned nanofiber meshes to further improve outgrowth speed and direction for application to peripheral nerve regeneration. Utilizing the insulating gap method discussed by our colleagues [10] and others [18], we successfully fabricated aligned nanofibers containing 10% laminin (FIG. 5A). A secondary benefit of alignment using this method is the stretching of nanofibers across the gap and resulting decrease in fiber diameter. In this case, we see significant stretching of fibers across the gap regardless of the initial total polymer concentration (5% or 8% w/v, both with laminin comprising 10% of the total polymer mass), pulling our average fiber diameter down to approximately 100 nm (FIG. 5B). In addition, we have characterized the alignment of these meshes using both manual calculations (FIG. 5C) and FFT (FIGS. 5D-F). Both indicate significantly greater alignment than nanofibers electrospun onto a grounded plate collector lacking the insulating gap, and minimal differences between laminin-PCL and PCL groups.

Rat Tibial Nerve Transection Recovery

To examine our blend and aligned meshes in the in vivo regenerative environment, we inserted the nanofiber meshes into PCL microfiber conduits, implanted them into the severed tibial nerve, and examined motor and sensory recovery over a six week timecourse. To assess the effects of both composition and geometry on recovery, we inserted meshes of PCL and laminin-PCL blend in random and longitudinal orientation. Because the tibial branch of the sciatic nerve is a mixed nerve, containing both motor and sensory fibers, we followed the animals' progress in recovery of both functions, as functional recovery is the critical outcome in patient care. Sham and empty conduit surgeries verified (1) the surgery itself does not result in functional deficit without severing the nerve, and (2) we successfully created a defect which would not heal during the course of our study.

In the present studies on thermal withdrawal latency (sensory function), no statistical differences were observed among the weeks of the sham surgery group (FIG. 6A). When comparing across experimental groups, PCL random, PCL aligned, and laminin-PCL random groups were significantly different from both the sham group and the laminin-PCL aligned group ($p<0.01$), and all groups were significantly different from the hollow group ($p<0.01$). In addition, PCL nanofibers, either random or aligned in configuration, had significantly lower latencies and faster recovery than the laminin-PCL random group ($p<0.01$). In considering the differences among the weeks of surgery, the most dramatic healing occurs between weeks four and five. Week four is significantly different from week six ($p<0.01$); however, latencies at weeks five and six are not significantly different ($p=0.322$). Individual group and week comparisons are indicated in FIG. 6A. Observing the overall trends, we found laminin-PCL aligned nanofibers to show latencies similar to sham surgeries across the timepoints, while nanofibers of the same composition but without alignment (laminin-PCL random) were more similar to hollow conduits. However, regardless of composition and orientation, all animals with nanofibers inside the conduit showed some recovery of function over the six week time period.

While improved sensory function is ideal, recovery of mechanical function is also of importance in the clinical setting, as complete mobility is desirable. With the tibial nerve transection injury, all animals were able to adapt and continue using both hind legs to ambulate. In addition, little self-mutilation of the injured foot was observed, suggesting this model is well-suited to study as the animals maintain relatively normal daily functioning capacity, but still show changes in gait analysis with injury which can be measured and applied to a modified tibial function index [17]. Animals with tibial nerve transections show shortening of both toe spread and intermediary toe spread, but little change in print length. For that reason, we compared toe spread, the distance between the first and fifth toes, across all groups and timepoints. All animals that received conduits with nanofibers show some return of function, while those with empty conduits show small changes in toe spread which may be a result of adaptation to the injured state, but no steady return to standard print features (FIG. 6B). A statistically significant difference was found between the group receiving PCL random nanofibers and the hollow control ($p=0.013$) or the 10% laminin blend random nanofibers ($p=0.011$). Laminin blend aligned nanofibers showed better healing when compared to hollow conduits ($p=0.062$) and to laminin blend random nanofibers ($p=0.66$); however, neither composition of randomly oriented fibers were significantly different from animals receiving hollow conduits. Individual groups and weeks were compared using Tukey's post hoc testing, but no significant differences were found, most likely due to the high variation in measurements.

Figure 7A:
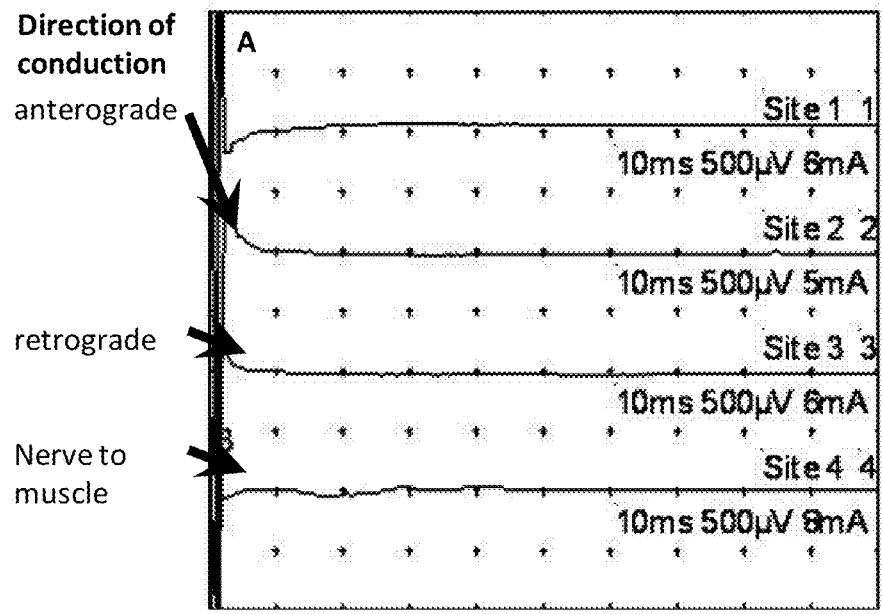
Figure 7B:
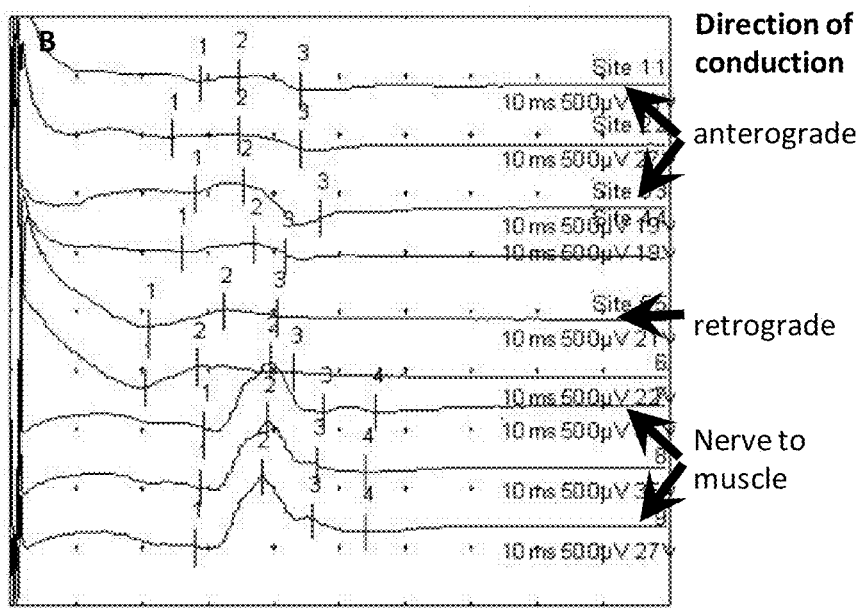
Figure 7C:
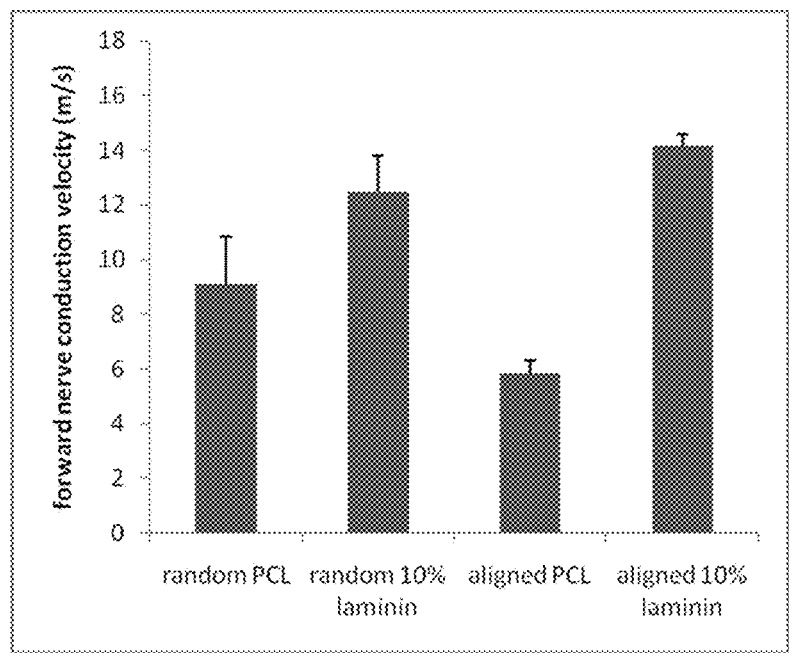
Figure 7D:
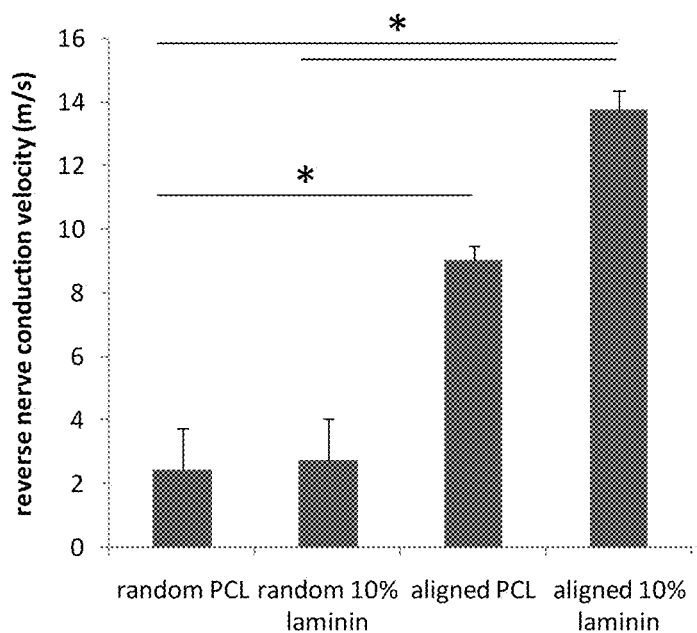
Figure 8A:
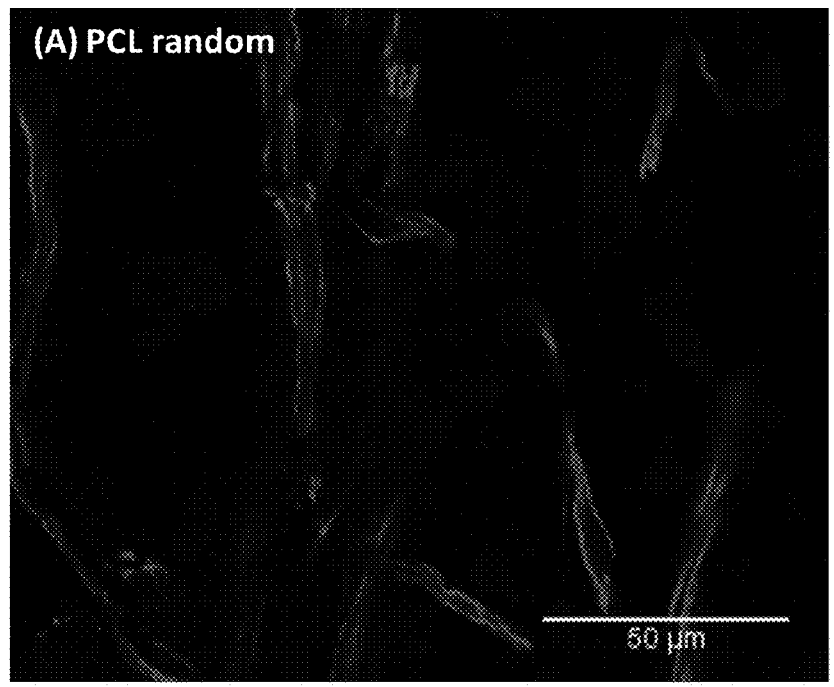
Figure 8B:
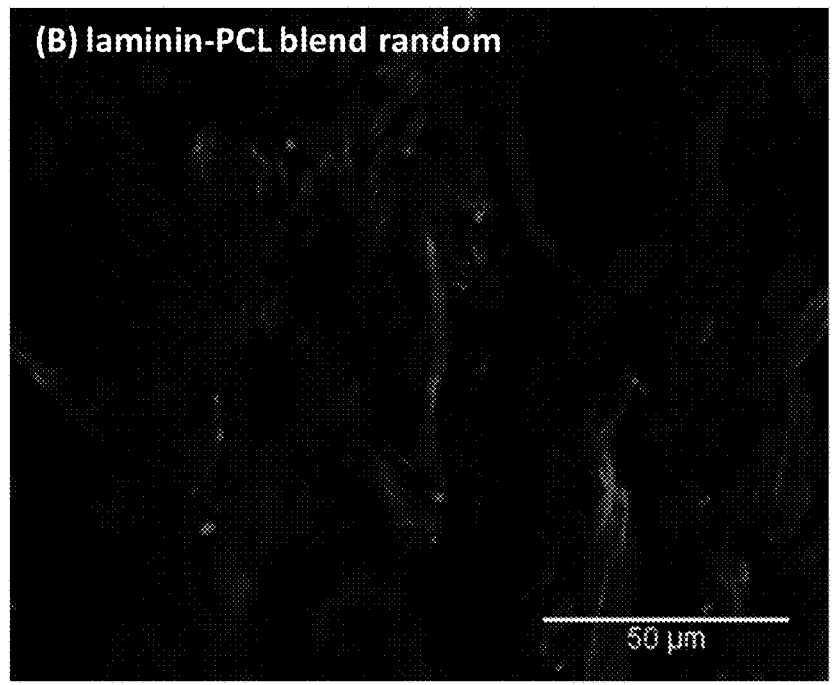
Figure 8C:
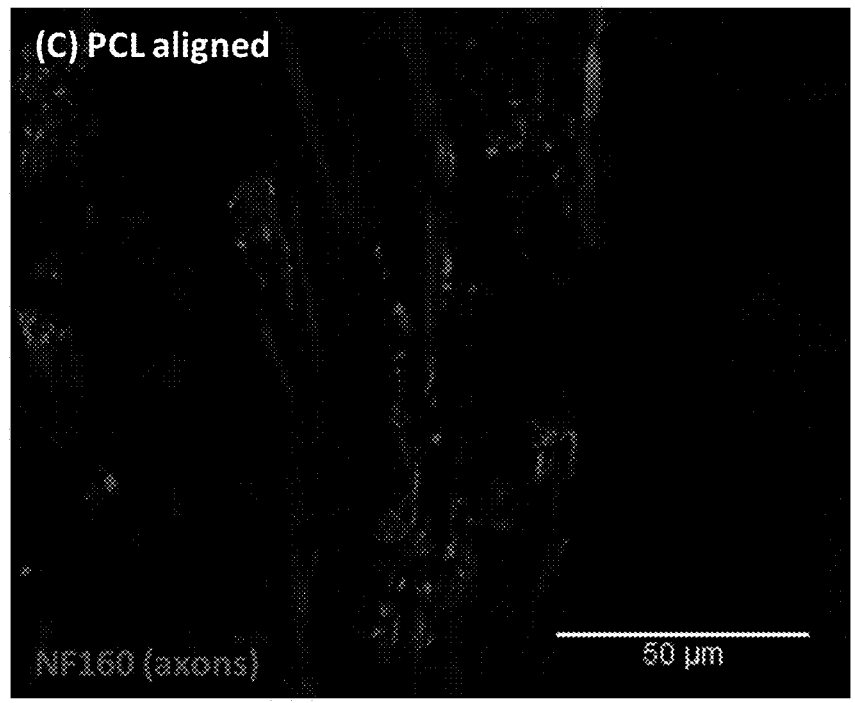
Figure 8D:
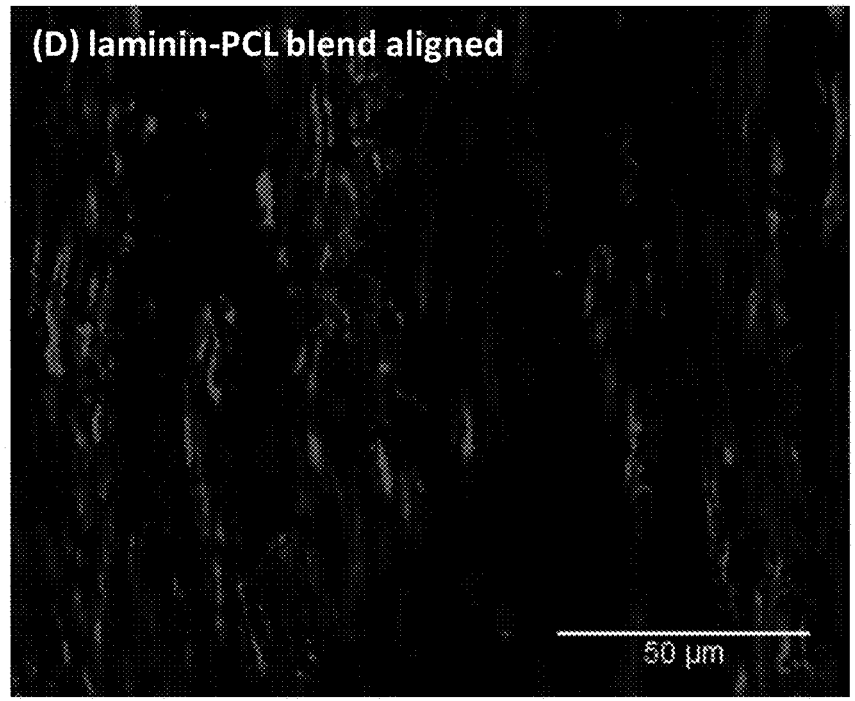

At the end of the six week study, the surgical site was re-opened for nerve conduction and electromyography assessment. Nerve conduction speeds across the healthy control tibial nerve in each animal were consistent with literature reported values [19]. Animals with no nanofibers within the lumen of the conduit showed no nerve conduction or muscle activity when the proximal or distal end of the severed nerve was stimulated; however, animals which received nanofibers within their conduits, regardless of the composition or orientation, showed some recovery of nerve-to-nerve and nerve-to-muscle conduction (FIG. 7A-C). When only retrograde conduction was considered, a significant difference was evident in conduits containing aligned nanofibers of either composition over those containing randomly oriented PCL or laminin-PCL blend nanofibers (FIG. 7D).

These results were supported by immunohistochemistry for regenerating axons (NF160). Representative images in FIG. 8 indicated some axonal outgrowth, represented by positive staining for NF160, an axonal marker, into conduits containing either composition of random nanofibers, though this outgrowth fails to show an appropriate linear organization from proximal to distal stump. In conduits which contained either composition of aligned nanofibers, greater tissue coverage and axonal outgrowth, indicated by positive NF160 staining, is apparent, and the tissue shows a level of organization in the longitudinal direction that does not exist in the other groups. The greatest axonal coverage occurred in the group receiving aligned laminin-PCL blend nanofibers, supporting the findings of the nerve conduction study and motor and sensory tests.

Discussion

Nerve transections are the model of choice among researchers studying peripheral nerve injury for two reasons: (1) lacerations resulting in nerve transections make up 30% of serious nerve injuries, and (2) injury and healing in this model are well characterized in both the research and clinical setting. In the distal portion of the injured nerve, Wallerian degeneration proceeds rapidly: axons and myelin fragment within hours of injury, and neurofilaments and tubes lose their ordered structure. With disruption of axonal continuity, all electrical conduction across the injury site is lost. Schwann cells achieve an activated state and function to aid macrophages in the removal and clearance of the injury site. In the proximal segment, degeneration proceeds similarly, but may be local (only affecting a small portion of the proximal segment) or may degenerate all the way to the axonal cell bodies. In transection injuries, regeneration only begins after Wallerian degeneration is complete, increasing the time to reinnervation and decreasing the probability of functional recovery [1]. For this reason, focus has been placed on increasing the speed and efficiency of axonal regeneration through biochemical and physical surface cues to aid healing and potentially recover function over larger gaps than previously thought possible.

Blend Fabrication and Characterization

Previously, we showed successful fabrication of laminin nanofibers and their utility for in vitro attachment and neurite extension. To improve processing capabilities, a synthetic, biodegradable polymer PCL was blended with laminin and blend nanofibers of similar dimensions were fabricated. FTIR spectroscopy confirmed the presence of both polymers in blend nanofibers, and analysis of the relative proportions, demonstrating production of blend nanofibers with specific laminin content. When compared with literature spectra for both PCL [20] and laminin [21], characteristic peaks of both polymers were evident, validating the blend fabrication methodology. This method of blending synthetic and natural polymers has been used with varying degrees of success by other groups using different polymer combinations [22], but we are the first to specifically electrospin blended PCL and laminin nanofibers for the purpose of enhancing axonal outgrowth in peripheral nerve repair.

Before examining the bioactivity of our laminin nanofibers, blend meshes were characterized to rule out other differences in the mesh characteristics which might affect cell behavior, such as mesh morphology, mechanical properties, and degradation rates. The blend nanofibers have mean fiber diameters ranging from 100-200 nm which is within the reported range of basement membrane [11]. These dimensions suggest that like pure laminin nanofibers, they can mimic the fiber geometry of the basement membrane. Tensile properties of the mesh were also equivalent regardless of laminin content of the mesh, mostly likely because the tensile strength of PCL is great enough to withstand such minimal additions of laminin. Uniaxial tensile properties are important a source of failure is due to tensile forces caused by patient movement beyond the bounds of the elastic region of the conduit. With all inner conduit materials maintaining no detectable differences in elastic modulus, yield strength, or UTS, we can be confident that minimal mechanical differences will not likely affect measured outcomes. In addition, the values we calculated for tensile properties are in agreement with the literature regarding PCL nanofibers [23]. Finally, the degradation rates found by GPC are consistent with published PCL degradation rates [24], and show no significant differences among groups over time. This data verifies that while laminin may prove a useful additive to these meshes, it does not affect the bulk degradation properties. Since all measured mesh characteristics remain consistent regardless of the laminin content, it is likely differences in cell behavior on the mesh are due specifically to the laminin content and mesh orientation.

Assessment of Bioactivity

For the purposes of these studies, laminin bioactivity is defined as the ability to promote cell attachment and neurite outgrowth. The bioactivity of various blends of laminin with PCL, in comparison to laminin nanofibers alone, was assayed with both PC12 cells and murine DRG. While it has typically been reported that substrate with nanotopography such as our nanofiber meshes will encourage greater cell attachment due to greater surface area, the presence of laminin was evaluated for deleterious or synergistic effects on cell attachment. We previously reported pure laminin nanofibers promote significantly greater and faster cell adhesion than laminin films [7], suggesting the relevance of the nanofiber geometry for attachment; however, in comparison with pure PCL nanofibers, even 10% laminin content provides for significantly greater cell attachment. Laminin therefore may be critical in encouraging faster regeneration in a multitude of settings, since cell adhesion is often a bottleneck step which impedes synthetic polymer success for tissue engineered scaffolds. In addition, Pierucci and colleagues cultured primary Schwann cells on PCL membranes, and found they do not attach as well as to PLLA membranes [25]. As Schwann cells actively secrete basal lamina and neurotrophic factors to modify the peripheral nerve microenvironment, especially after injury and during regeneration, Schwann cell attachment is crucial to successful regeneration. The addition of laminin to PCL nanofibers should improve Schwann cell attachment, which in turn increases basal lamina secretion and the production of neurotrophic factors which support and guide the regenerating axon. While these studies examined PC12 cell attachment as a representative measurement of how cells will likely behave on the mesh, future studies will explore how primary Schwann cells respond to the composition and alignment of the mesh.

While successful cell adhesion to our scaffold is crucial, we hope to utilize the intrinsic neurite promoting properties of laminin to encourage outgrowth beyond what is obtainable with synthetic polymers. Several groups have reported the necessity for axonal adhesion to the growth surface in order to produce the engorgement of growth cones and subsequent formation of a new axonal length [26,27]. Observed PC12 cell and murine DRG attachment and neurite extension support this conclusion regarding laminin blend nanofiber substrates. We observed greater neurite length from DRG on laminin substrates, as well as a greater percentage of PC12 cells extending processes with or without NGF stimulation. These data lead us to conclude that while there may be cases where adhesion to a substrate is detrimental, in the case of laminin, which contains specific axonal outgrowth and growth cone guidance domains, cell or neurite attachment does not prohibit outgrowth. In fact, we find laminin content at or above 10% total polymer weight enhances the capacity for process outgrowth.

Oriented Nanofiber Meshes and Directional Outgrowth

Schwann cells can secrete and maintain two different structures of laminin: a fibrillar construct typically indicative of young Schwann cells or low-passage cells in vitro, and a reticular construct more often seen with higher-passage cells or mature Schwann cells [28]. Because the fibrillar matrix state exists during development, it is highly probable this fibrillar laminin mesh provides important path-finding cues for the growth cones of developing neurons. By extension, this fibrillar structure may be particularly relevant in regeneration as it mimics the environment during development which may function to speed the regenerative capability of the peripheral nervous system. In our studies, we found attachment to be equivalent on aligned substrates and on random nanofiber substrates. In particular, no differences were found with attachment on aligned fibers even when laminin was not included in the mesh. Since previous studies showed attachment to laminin-containing nanofibers as preferential over PCL only nanofibers, these data suggest that structural orientation as well as biochemical cues play critical roles in cell attachment.

Rat Tibial Nerve Transection Recovery

With respect to functional recovery, we assessed motor and sensory function throughout the study, in addition to nerve conduction velocity, electromyography, and tissue histology at the end of the study. In animals receiving empty conduits, little improvement is seen in either motor or sensory function, validating the 10 mm defect as a large gap that will not heal successfully within six weeks. In addition, significant reduction in thermal withdrawal latency was observed with all conduits containing nanofibers, with laminin-PCL aligned nanofibers providing the best recovery through the first four weeks of the study. While this test is subject to some variability based on the environment, care was taken to maintain as many external variables constant as possible over the course of the study. The decreasing standard deviations over time, especially in the sixth week of the study, show that while individual animal response to the surgery may vary initially, healing responses have stabilized by the sixth week. By that time, most animals showed thermal withdrawal latency in the pre-operative range of 4-6 seconds. The decreasing trends in thermal withdrawal latency, as well as the companion decrease in withdrawal deviation suggests that a physical, nano-scale presence within the lumen of the conduit promotes faster outgrowth and functional recovery, regardless of the composition or orientation. Statistical differences in healing occur between weeks five and six across all groups, as latencies decrease to near un-operated response. While in this case thermal withdrawal latency was tested weekly, testing more often might elucidate a more exact point at which all animals return to their baseline levels. We expected to find laminin nanofibers within the conduit providing an ideal substrate for axonal attachment and extension; however, the latency data suggests alignment of nanofibers may be more critical than composition. Both PCL and laminin-PCL aligned nanofibers showed faster recovery to normal response than either composition of random nanofibers. In addition, laminin-PCL random nanofibers showed the slowest recovery of function. This surprising result may be due to the potential immunogenicity of laminin in this model. It is possible healing that is complicated by the animals' immune reaction to the foreign protein, slowing initial healing but still allowing the animal to reach baseline latency levels by the end of six weeks Motor recovery was assessed by gait over time from pre-operative tracks as well as the un-operated control side. In this assessment, differences in motor recovery emerged based on the content and alignment of nanofibers within the conduit. Regardless of composition or orientation, nanofibers within the conduit provided for better recovery capabilities than a hollow conduit. When comparing the toe spread, animals receiving PCL nanofibers in the aligned configuration showed the most significant motor recovery when compared to hollow conduits, whereas randomly-oriented laminin nanofibers showed no significant difference in recovery over hollow conduits. In addition, conduits containing laminin blend aligned nanofibers approached significance when compared to hollow conduits and those containing randomly-oriented laminin blend nanofibers. These results suggest substrate alignment is critical for motor recovery. In this case, animals receiving randomly-oriented nanofibers with laminin content showed minimal functional recovery over hollow conduits. Over the short duration of this study, it is possible the animals' immune system was still mounting a response to the laminin content in the conduit, causing slightly greater inflammation in those surgery sites and affecting the animals' gait. However, when considering aligned conduits, perhaps the benefit of alignment outweighs any potential inflammatory effects of laminin, allowing animals with aligned laminin blend conduits to approach or in some cases surpass the functional recovery of animals that received aligned PCL nanofibers.

When examining the ability of regenerated nerves to conduct impulses, we measured conduction both anterograde and retrograde. While trends were apparent in anterograde conduction, no significance was found; however, anterograde conduction is especially sensitive to outside interference. For example, if any extraneous tissue is not freed from the nerve, conduction is possible anterograde through the adhered muscle tissue. Fortunately, retrograde transmission is not as susceptible to this particular noise, and in this metric there are significant differences in nerve conduction velocity. As previously discussed, the presence of nanofibers within the lumen of the conduit does indeed promote faster outgrowth and greater functional recovery in terms of nerve conduction at the six week time point. Randomly oriented synthetic nanofibers provide a better surface than an empty conduit. However, regardless of composition, conduits containing aligned nanofibers demonstrated significantly greater reverse conduction velocities. The highest mean conduction velocity was achieved with laminin-PCL aligned nanofibers, perhaps because this construct most closely mimics both the structure (alignment) and composition (laminin content) of the native healing environment.

Conclusions

In conclusion, laminin-PCL blend nanofibers containing 10% by weight laminin maintain the bioactivity of pure laminin nanofibers in terms of cell adhesion and neurite extension. Alignment of nanofibers further increases the length of process extension. When used in the lumen of a conduit for peripheral nerve regeneration, the nanofiber structure provides significant benefit over a hollow conduit, with even greater benefit and faster healing seen with laminin content, and the fastest healing with alignment along the length of the conduit. These studies provide a firm foundation for the use of natural-synthetic blend electrospun nanofibers to enhance existing hollow nerve guidance conduits. The similarity in surgical technique and obvious benefit to the patient should lead to faster translation into clinical application.

Other methods which were used but not described herein are well known and within the competence of one of ordinary skill in the art of cell biology, molecular biology, and clinical medicine. The invention should not be construed to be limited solely to the assays and methods described herein, but should be construed to include other methods and assays as well. One of skill in the art will know that other assays and methods are available to perform the procedures described herein.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

Bibliography

1. Burnett M G, Zager E L. Pathophysiology of peripheral nerve injury: a brief review. Neurosurg Focus 2004; 16(5):E1. Review.

2. Colen K L, Choi M, Chiu D T. Nerve grafts and conduits. Plast Reconstr Surg 2009; 124(6 Suppl):e386-94.

3. Bellamkonda R V. Peripheral nerve regeneration: an opinion on channels, scaffolds and anisotropy. Biomaterials 2006; 27(19):3515-8.

4. Hoke A. Mechanisms of Disease: what factors limit the success of peripheral nerve regeneration in humans? Nat Clin Pract Neurol 2006; 2(8):448-54. Review 5. Jiang X, Lim S H, Mao H Q, Chew S Y. Current applications and future perspectives of artificial nerve conduits. Exp Neurol 2010; 223(1):86-101.

6. Kleinman H K, Philp D, Hoffman M P. Role of the extracellular matrix in morphogenesis. Curr Opin Biotechnol 2003; 14:526-532.

7. Neal R A, McClugage S G, Link M C, Sefcik L S, Ogle R C, Botchwey E A. Laminin nanofiber meshes that mimic morphological properties and bioactivity of basement membranes. Tissue Eng Part C Methods 2009; 15(1):11-21.

8. Clements I P, Kim Y T, English A W, Lu X, Chung A, Bellamkonda R V. Thin-film enhanced nerve guidance channels for peripheral nerve repair. Biomaterials 2009; 30(23-24):3834-46.

9. Kim Y T, Haftel V K, Kumar S, Bellamkonda R V. The role of aligned polymer fiber-based constructs in the bridging of long peripheral nerve gaps. Biomaterials 2008; 29(21):3117-27.

10. Chaurey V, Chiang P, Polanco C, Su Y, Chou C, Swami N. Design rules for insulator gaps on patterned collectors for alignment of sub-100 nm electrospun nanofibers. Submitted.

11. Abrams G A, Schaus S S, Goodman S L, Nealey P F, Murphy C J. Nanoscale topography of the corneal epithelial basement membrane and Descemet's membrane of the human. Cornea. 2000; 19:57-64.

12. Kakade M V, Givens S, Gardner K, Lee K H, Chase D B, Rabolt J F. Electric field induced orientation of polymer chains in macroscopically aligned electrospun polymer nanofibers. J Am Chem Soc 2007; 129(10):2777-82.

13. Hannan G N, Reilly W. Adsorption from fetal calf serum of collagen-like proteins which bind fibronectin and promote cell attachment. Exp Cell Res 1988; 178(2):343-57.

14. Bethea C L, Borg T K. PC12 cell aggregation and dopamine production on EHS-derived extracellular matrix. Mol Cell Endocrinol 1988; 58(2-3):113-28.

15. Liu L, Geisert E E, Frankfurter A, Spano A J, Jiang C X, Yue J, et. al. A transgenic mouse class-III beta tubulin reporter using yellow fluorescent protein. Genesis 2007; 45(9):560-9.

16. Jiang M, Zhuge X, Yang Y, Gu X, Ding F. The promotion of peripheral nerve regeneration by chitooligosaccharides in the rat nerve crush injury model. Neurosci Lett 2009; 454(3):239-43.

17. Bain J R, Mackinnon S E, Hunter D A. Functional evaluation of complete sciatic, peroneal and posterior tibial nerve lesions in the rat. Plast Reconstruct Surg 1989; 83:129-136.

18. Li D, Wang Y L, Xia Y N. Electrospinning of polymeric and ceramic nanofibers as uniaxially aligned arrays. Nano Letters 2003; 8:1167-1171.

19. Wei S Y, Zhang P X, Han N, Dang Y, Zhang H B, Zhang D Y, et. al. Effects of Hedysari polysaccharides on regeneration and function recovery following peripheral nerve injury in rats. Am J Chin Med. 2009; 37(1):57-67.

20. Elzein T, Nasser-Eddine M, Delaite C, Bistac S, Dumas P. FTIR study of polycaprolactone chain organization at interfaces. J Colloid Interface Sci 2004; 273(2):381-7.

21. Huang Y C, Huang C C, Huang Y Y, Chen K S. Surface modification and characterization of chitosan or PLGA membrane with laminin by chemical and oxygen plasma treatment for neural regeneration. J Biomed Mater Res A 2007; 82(4): 842-51.

22. Li M, Mondrinos M J, Chen X, Lelkes P I. Electrospun blends of natural and synthetic polymers as scaffolds for tissue engineering. Conf Proc IEEE Eng Med Biol Soc 2005; 6:5858-61.

23. Lee K H, Kim H Y, Khil M S, Lee D R. Characterization of nano-structured poly(-caprolactone) nonwoven mats via electrospinning Polymer 2003; 44(4):1287-1294.

24. Pektok E, Nottelet B, Tille J C, Gurny R, Kalangos A, Moeller M, Walpoth B H. Degradation and healing characteristics of small-diameter poly(epsilon-caprolactone) vascular grafts in the rat systemic arterial circulation. Circulation 2008; 118(24):2563-70.

25. Pierucci A, Duek E A, de Oliveira A L. Expression of basal lamina components by Schwann cells cultured on poly (lactic acid) (PLLA) and poly(caprolactone) (PCL) membranes. J Mater Sci Mater Med 2009; 20(2):489-95.

26. Ketschek A R, Jones S L, Gallo G. Axon extension in the fast and slow lanes: substratum-dependent engagement of myosin II functions. Dev Neurobiol 2007; 67(10):1305-20.

27. Varnum-Finney B, Reichardt L F. Vinculin-deficient PC12 cell lines extend unstable lamellipodia and filopodia and have a reduced rate of neurite outgrowth. J Cell Biol 1994; 127(4):1071-84.

28. Tsiper M V, Yurchenco P D. Laminin assembles into separate basement membrane and fibrillar matrices in Schwann cells. J Cell Sci 2002; 115(Pt 5):1005-15.

What is claimed is:

1. A method for treating an injured tibial nerve, said method comprising contacting said injured nerve with nanofibers electrospun from a mixture of a protein and a polymer, wherein said protein is laminin and said polymer is polycaprolactone (PCL), further wherein said mixture is prepared in 1,1,1,3,3,3-hexafluoro-2-propanol (HFP), thereby treating an injured tibial nerve.

2. The method of claim 1, wherein said nanofibers are on a substrate, further wherein said nanofibers are aligned, and said substrate comprising nanofibers is a conduit.

3. The method of claim 1, wherein said mixture comprises about 10% laminin weight to weight of total protein and PCL.

4. The method of claim 1, wherein said injured tibial nerve has been transected and said method stimulates regeneration of said injured nerve.

5. The method of claim 1, wherein said method stimulates neurite extension.

6. The method of claim 1, wherein said method stimulates the recovery of sensory function in said nerve.

7. The method of claim 1, wherein said method stimulates the recovery of motor function in said nerve.

8. The method of claim 1, wherein said method stimulates the recovery of nerve conduction velocity in said nerve.

9. The method of claim 1, wherein said method stimulates axonal regeneration.

10. The method of claim 1, wherein the laminin and PCL mixture is prepared for electrospinning at a weight to volume total percentage of about 1% to about 70%.

11. The method of claim 1, wherein the laminin and PCL mixture is prepared at a weight to volume total percentage of about 1% to about 20%.

12. The method of claim 11, wherein the laminin and PCL mixture is prepared at a weight to volume total percentage of 5% or 8% laminin+PCL.

13. The method of claim 12, wherein the amount of laminin to PCL in the mixture prepared for eleetrospinning is about 0.1% to about 20% weight to weight.

14. The method of claim 1, wherein said laminin is dissolved at a concentration ranging from about 0.1% weight to volume to about 50% weight to volume.

15. The method of claim 14, wherein said laminin is dissolved at a concentration ranging from about 1.0% weight to volume to about 10% weight to volume.

16. The method of claim 1, wherein said nanofibers comprise diameters of about 10 nm to about 1,000 nm.

17. The method of claim 2, wherein said nanofibers comprise diameters of about 100 nm to about 300 nm.

18. The method of claim 1 wherein said injured nerve is contacted with a sheet of said nanofibers electrospun from sad mixture of protein and PCL.

19. The method of claim 18, wherein said sheet is multilayered.

20. The method of claim 19, wherein said multilayered sheet comprises at least two layers of nanofibers.

21. The method of claim 20, wherein said multilayered sheet comprises at least three layers of nanofibers.

22. The method of claim 18, wherein said nanofibers are aligned.

23. The method of claim 18, wherein said sheet farther comprises at least one growth factor.

24. The method of claim 23, wherein the at least one growth factor is selected from the group consisting of vascular endothelial growth factor, transforming growth factor-beta, transforming growth factor-alpha, epidermal growth factor, endothelial growth factor, platelet-derived growth factor, nerve growth factor, fibroblast growth factor, and insulin growth factor.

25. The method of claim 24, wherein the sheet releases said at least one growth factor.

* * * * *